US012637511B2

(12) United States Patent (10) Patent No.: US 12,637,511 B2
Forget et al. (45) Date of Patent: May 26, 2026

(54) METHODS FOR EXPANSION OF TUMOR INFILTRATING LYMPHOCYTES AND USE THEREOF

(71) Applicant: Board of Regents, The University of Texas System, Austin, TX (US)

(72) Inventors: Marie-Andrée Forget, Houston, TX (US); Chantale Bernatchez, Houston, TX (US); Cara Haymaker, Houston, TX (US); Michael A Curran, Houston, TX (US); Patrick Hwu, Houston, TX (US); Cassian Yee, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 868 days.

(21) Appl. No.: 17/904,479

(22) PCT Filed: Feb. 16, 2021

(86) PCT No.: PCT/US2021/018252
§ 371 (c)(1),
(2) Date: Aug. 17, 2022

(87) PCT Pub. No.: WO2021/167908
PCT Pub. Date: Aug. 26, 2021

(65) Prior Publication Data
US 2023/0106973 A1 Apr. 6, 2023

Related U.S. Application Data

(60) Provisional application No. 62/977,672, filed on Feb. 17, 2020.

(51) Int. Cl.
| | |
|---|---|
| *C07K 16/28* | (2006.01) |
| *A61K 40/11* | (2025.01) |
| *A61K 40/42* | (2025.01) |
| *A61P 35/00* | (2006.01) |
| *C07K 14/55* | (2006.01) |
| *C07K 14/705* | (2006.01) |
| *C07K 14/725* | (2006.01) |
| *C12N 5/0783* | (2010.01) |

(52) U.S. Cl.
CPC .......... *C07K 16/2809* (2013.01); *A61K 40/11* (2025.01); *A61K 40/428* (2025.01); *A61P 35/00* (2018.01); *C07K 14/55* (2013.01); *C07K 14/7051* (2013.01); *C07K 14/70596* (2013.01); *C07K 16/2878* (2013.01); *C12N 5/0636* (2013.01); *C12N 5/0638* (2013.01)

(58) Field of Classification Search
CPC ............ C07K 16/2809; C07K 2317/75; A61K 40/11; A61P 35/00; C12N 5/0636
See application file for complete search history.

(56) References Cited

U.S. PATENT DOCUMENTS

| | | | |
|---|---|---|---|
| 5,827,642 | A | 10/1998 | Riddell et al. |
| 10,308,709 | B2 | 6/2019 | Tu et al. |
| 2004/0058445 | A1 | 3/2004 | Ledbetter et al. |
| 2008/0112951 | A1 | 5/2008 | Phalipon et al. |
| 2009/0098140 | A1 | 4/2009 | Grompe et al. |
| 2014/0086913 | A1 | 3/2014 | Smith et al. |
| 2014/0154254 | A1 | 6/2014 | Kannan et al. |
| 2015/0133640 | A1 | 5/2015 | Blein et al. |
| 2015/0147333 | A1 | 5/2015 | Storm et al. |
| 2017/0044496 | A1 | 2/2017 | Sarnaik et al. |
| 2023/0092390 | A1 | 3/2023 | Curran et al. |
| 2023/0106973 | A1 | 4/2023 | Forget et al. |

FOREIGN PATENT DOCUMENTS

| | | | |
|---|---|---|---|
| WO | WO 2010/113117 | A2 | 10/2010 |
| WO | WO 2010/138803 | A2 | 12/2010 |
| WO | WO 2015/189638 | A2 | 12/2015 |
| WO | WO 2016/131125 | A1 | 8/2016 |
| WO | WO 2017/205745 | A1 | 11/2017 |
| WO | WO 2019/136459 | A1 | 7/2019 |
| WO | WO 2019/141268 | A1 | 7/2019 |
| WO | WO 2019/190579 | A1 | 10/2019 |
| WO | WO 2019/210131 | A1 | 10/2019 |
| WO | WO 2020/011968 | A1 | 1/2020 |

OTHER PUBLICATIONS

Bartkowiak, T. et al., "4-1BB agonists: multi-potent potentiators of tumor immunity," *Frontiers in Oncology*, 5.117 (2015): 1-16.
Chacon, J. A. et al., "Co-Stimulation through 4-1BB/CD137 Improves the Expansion and Function of CD8+ Melanoma Tumor-Infiltrating Lymphocytes for Adoptive T-Cell Therapy," *Plos One*, 8.4 (2013): e60031, 1-14.
Chapuis, A. G. et al., "Transferred Melanoma-Specific CD8+ T Cells Persist, Mediate Tumor Regression and Acquire Central Memory Phenotype," *PNAS*, 109.12 (2012): 4592-4597.
Creasy, C. A. et al., "Exposure to anti-PD-1 causes functional differences in tumor-infiltrating lymphocytes in rare solid tumors," *Eur J Immunol*, 49 (2019): 2245-2251.

(Continued)

*Primary Examiner* — Valerie E Bertoglio
(74) *Attorney, Agent, or Firm* — pH IP Law

(57) ABSTRACT

Provided herein are methods for the activation and expansion of genetically-modified Tcells, such as tumor infiltrating lymphocytes. In some cases, cells of the embodiments can be used for the therapeutic treatment of human diseases, such as cancer.

18 Claims, 5 Drawing Sheets

Specification includes a Sequence Listing.

(56) References Cited

OTHER PUBLICATIONS

Dudley, M. E. et al. "Adoptive cell transfer therapy following non-myeloablative but lymphodepleting chemotherapy for the treatment of patients with refractory metastatic melanoma," *Journal of Clinical Oncology*, 23.10 (2005): 2346-2357.

Extended European Search Report issued in European Patent Application No. 21757958.0, dated Jun. 4, 2024.

Forget, M.-A. et al., "A Novel Method to Generate and expand Clinical-Grade, Genetically Modified, tumor-Infiltrating Lymphocytes," *Frontiers in Immunology*, 8.908 (2017): 1-8.

Forget, M. A. et al., "Prospective Analysis of Adoptive TIL Therapy in Patients with Metastatic Melanoma: Response, Impact of Anti-CTLA4, and Biomarkers to Predict Clinical Outcome," *Clin Cancer Res*, 24.18 (2018): 4416-4428.

Grimm, E. A. et al., "Characterization of interleukin-2-initiated versus OKT3-initiated human tumor-infiltrating lymphocytes from glioblastoma multiforme: growth characteristics, cytolytic activity, and cell phenotype," *Cancer Immunol Immunother*., 32 (1991): 391-399.

Harao, M. et al., "4-1BB-enhanced expansion of CD8+ TIL from triple-negative breast cancer unveils mutation-specific CD8+ T cells," *Cancer Immunol Res.*, 5.6 (2017): 439-445.

Lutsiak, M. E. C. et al., "Inhibition of CD4($^+$)25$^+$ T regulatory cell function implicated in enhanced immune response by low-dose cyclophosphamide," *Blood*, 105.7 (2005): 2862-2868.

Maguire, H. C. et al., "Enhancement of dinitrochlorobenzene (DNCB) contact sensitization by cyclophosphamide in the guinea pig," *The Journal of Investigative Dermatology*, 48.1 (1967): 39-43.

Mardiana, S. et al., "A Multifunctional Role for Adjuvant Anti-4-1BB Therapy in Augmenting Antitumor Response by Chimeric Antigen Receptor T Cells," *Cancer Research*, 77.6 (2017): 1296-1309.

Martinez, O. M. et al., "IL-4 inhibits IL-2 receptor expression and IL-2-dependent proliferation of human T cell," *The Journal of Immunology*, 144 (1990): 2211-2215.

Nielson, M. et al., "Preclinical development of tumor-infiltrating lymphocyte (TIL) based adoptive cell transfer (ACT) immunotherapy for patients with sarcoma and the potential benefit of anti-CD137 stimulation," *J Clin Oncol.*, 35 (2017): abstract No. e14545.

Partial European Search Report issued in European Patent Application No. 21757958.0, dated Mar. 11, 2024.

PCT International Search report and Written Opinion issued in International Patent Application No. PCT/US2021/018276, mailed Jun. 23, 2021.

PCT International Preliminary Report on Patentability issued in International Patent Application No. PCT/US2021/018276, mailed Sep. 1, 2022.

PCT International Search report and Written Opinion issued in International Patent Application No. PCT/US2021/018252, mailed May 14, 2021.

PCT International Preliminary Report on Patentability issued in International Patent Application No. PCT/US2021/018252, mailed Sep. 1, 2022.

Qi, X. et al., "Optimization of 4-1BB antibody for cancer immunotherapy by balancing agonistic strength with FcyR affinity," *Nature Communications*, 10 (2019): 2141, 1-11.

Quezada, S. A. et al., "CTLA4 blockade and GM-CSF combination immunotherapy alters the intratumor balance of effector and regulatory T cells," *The Journal of Clinical Investigation*, 116.7 (2006): 1935-1945.

Rabu, C. et al., "Production of Recombinant Human Trimeric CD137L (4-1BBL)," *The Journal of Biological Chemistry*, 280.50 (2005): 41472-41481.

Radvanyi, L. G. et al., "Specific lymphocyte subsets predict response to adoptive cell therapy using expanded autologous tumor-infiltrating lymphocytes in metastatic melanoma patients," *Clin Cancer Res*, 18.24 (2012): 6758-6770.

Sakellariou-Thompson, D. et al., "4-1BB agonist focuses CD8+ tumor-infiltrating T-cell growth into a distinct repertoire capable of tumor recognition in pancreatic cancer," *Clin Cancer Res.*, 23.23 (2017): 7263-7275.

Sakellariou-Thompson, D. et al., "Potential clinical application of tumor-infiltrating lymphocyte therapy for ovarian epithelial cancer prior or post-resistance to chemotherapy," *Cancer Immunology, Immunotherapy*, 68 (2019): 1747-1757.

Shah, P. et al., "Combined IL-2, agonistic CD3 and 4-1BB stimulation preserve clonotype hierarchy in propagated non-small cell lung cancer tumor-infiltrating lymphocytes," *J Immunother Cancer*, 10 (2022): e003082, 1-14.

Somerville, R. P. T. et al., "Clinical scale rapid expansion of lymphocytes for adoptive cell transfer therapy in the WAVE® bioreactor," *The Journal of Translational Medicine*, 10.69 (2012): 1-11.

Sutmuller, R. P. et al., "Synergism of cytotoxic T lymphocyte-associated antigen 4 blockade and depletion of CD25(+) regulatory T cells in antitumor therapy reveals alternative pathways for suppression of autoreactive cytotoxic T lymphocyte responses," *J Exp Med.*, 194.6 (2001): 823-832.

Tavera, R. J. et al., "Utilizing T-cell Activation Signals 1, 2, and 3 for Tumor-infiltrating Lymphocytes (TIL) Expansion: The Advantage Over the Sole Use of Interleukin-2 in Cutaneous and Uveal Melanoma," *J Immunother.*, 41.9 (2018): 399-405.

Tsoukas, C. D. et al., "Activation of resting T lymphocytes by anti-CD3 (T3) antibodies in the absence of monocytes," *The Journal of Immunology*, 135 (1985): 1719-1723.

Vinay, D. S. et al., "Immunotherapy of Cancer with 4-1BB," *Molecular Cancer Therapeutics*, 11.5 (2012): 1062-1070.

Vormittag, P. et al., "A guide to manufacturing CAR T cell therapies," *Current Opinion in Biotechnology*, 53 (2018): 164-181.

Weber, J. et al., "White Paper on Adoptive Cell Therapy for Cancer with Tumor-Infiltrating Lymphocytes: A Report of the CTEP Subcommittee on Adoptive Cell Therapy," *Clinical Cancer Research*, 17.7 (2011): 1664-1673.

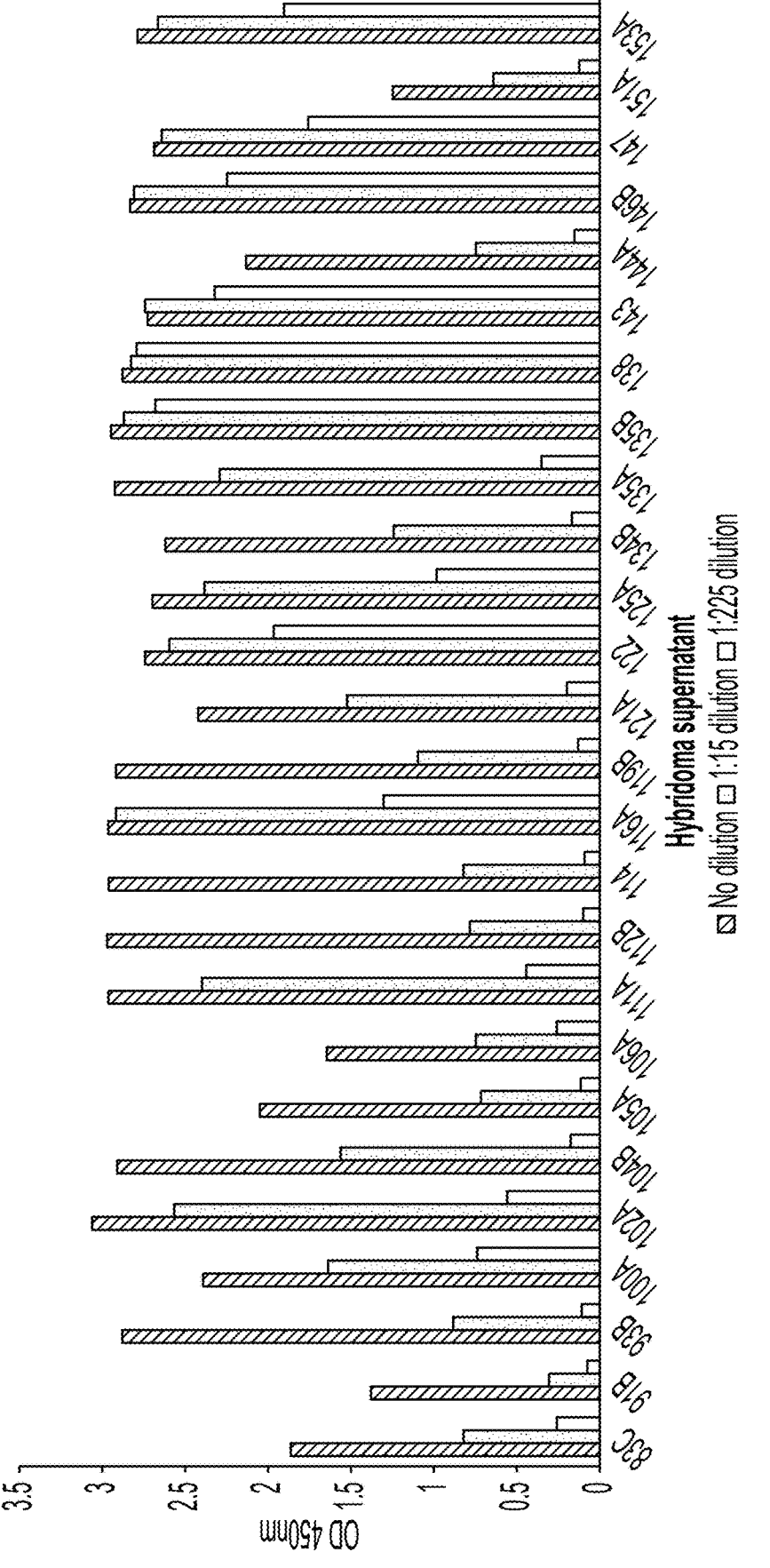
FIG. 2A-cont.

METHODS FOR EXPANSION OF TUMOR INFILTRATING LYMPHOCYTES AND USE THEREOF

This application is a national phase application under 35 U.S.C. § 371 of International Application No. PCT/US2021/018252, filed Feb. 16, 2021, which claims the benefit of U.S. Provisional Patent Application No. 62/977,672, filed Feb. 17, 2020, each of which is incorporated herein by reference in its entirety.

This invention was made with government support under grant number CA016672 awarded by the National Institutes of Health. The government has certain rights in the invention.

INCORPORATION OF SEQUENCE LISTING

The sequence listing that is contained in the file named "UTFCP1482WO_ST25.txt", which is 23 KB (as measured in Microsoft Windows®) and was created on Feb. 16, 2021, is filed herewith by electronic submission and is incorporated by reference herein.

BACKGROUND

1. Field

The present invention relates generally to the field of molecular biology. More particularly, it concerns methods of expanding tumor-infiltrating lymphocytes.

2. Description of Related Art

The potential of tumor-infiltrating therapy (TIL) therapy has been shown in melanoma by multiple cancer centers. Because of the wide diversity of tumor antigen-specific cells (encompassing both self and mutated) that TIL therapy offers, efforts are being made to transpose this success to other types of solid tumors, as found in gastric, cervical, and ovarian cancers. One of the major challenges faced in these new trials is the difficulty of expanding the CD8T cells from within the TIL population (Harao et al., 2017; Sakellariou-Thompson et al., 2017; Sakellariou et al., 2019). Thus, there is an unmet need for improved methods of expanding TILs, such as for the treatment of various solid cancers, including breast cancer, pancreatic cancer and ovarian cancer.

SUMMARY

In certain embodiments, the present disclosure provides an ex vivo method for activation and expansion of T cells comprising: (a) pre-activating a starting population of T cells in the presence of an agonistic 4-1BB antibody and an anti-CD3 antibody to generate pre-activated T cells; (b) further activating the pre-activated T cells in the absence of an agonistic 4-1BB antibody to generate activated T cells; (c) genetically modifying the activated T cells to obtain genetically modified T cells; and (d) expanding the genetically modified T cells in the presence of IL-2 and feeder cells to produce a population of expanded T cells.

In some aspects, the starting population of T cells is derived from tumor tissue. In certain aspects, the starting population of T cells comprises tumor infiltrating lymphocytes (TILs). In some aspects, pre-activating is further in the presence of IL-2. In particular aspects, the IL-2 is human recombinant IL-2. In some aspects, the human recombinant IL-2 is at a concentration of 1,000 IU/mL to 10,000 IU/mL, such as 2000, 3000, 4000, 5000, 6000, 7000, 8000, 9000, or 10000 IU/mL. In particular aspects, the human recombinant IL-2 is a concentration of 6,000 IU/mL. In some aspects, the anti-CD3 antibody is at a concentration of 10 ng/mL to 50 ng/mL, such as 10, 15, 20, 25, 30, 35, 40, 45, or 50 ng/mL. In particular aspects, the anti-CD3 antibody is at a concentration of 30 ng/mL. In certain aspects, the agonistic 4-1BB antibody is at a concentration of 1-20 μg/mL, such as 1, 5, 10, 15, or 20 μg/mL. In specific aspects, the agonistic 4-1BB antibody is at a concentration of 10 μg/mL.

In some aspects, pre-activating is performed for 10-16 days, such as for 10, 11, 12, 13, 14, 15, or 16 days. In certain aspects, pre-activating is performed for 14 days. In certain aspects, pre-activating is performed in a bioreactor, such as a gas-permeable bioreactor. For example, the gas-permeable bioreactor is a G-Rex 10 bioreactor. In some aspects, half media changes are performed every 3 to 4 days.

In certain aspects, the agonistic 4-1BB antibody is an isolated monoclonal antibody, wherein the antibody specifically binds to 4-1BB and comprises: (a) a first $V_H$ CDR is identical to SEQ ID NO: 3; (b) a second $V_H$ CDR is identical to SEQ ID NO: 5; (c) a third $V_H$ CDR is identical to SEQ ID NO: 7; (d) a first $V_L$ CDR is identical to SEQ ID NO: 11; (e) a second $V_L$ CDR is identical to SEQ ID NO: 13; and (f) a third $V_L$ CDR is identical to SEQ ID NO: 15; or m(a) a first $V_H$ CDR is identical to SEQ ID NO: 19; (b) a second $V_H$ CDR is identical to SEQ ID NO: 21; (c) a third $V_H$ CDR is identical to SEQ ID NO: 23; (d) a first $V_L$ CDR is identical to SEQ ID NO: 27; (e) a second $V_L$ CDR is identical to SEQ ID NO: 29; and (f) a third $V_L$ CDR is identical to SEQ ID NO: 31; or (a) a first $V_H$ CDR is identical to SEQ ID NO: 35; (b) a second $V_H$ CDR is identical to SEQ ID NO: 37; (c) a third $V_H$ CDR is identical to SEQ ID NO: 39; (d) a first $V_L$ CDR is identical to SEQ ID NO: 43; (e) a second $V_L$ CDR is identical to SEQ ID NO: 45; and (f) a third $V_L$ CDR is identical to SEQ ID NO: 47; or (a) a first $V_H$ CDR is identical to SEQ ID NO: 51; (b) a second $V_H$ CDR is identical to SEQ ID NO: 53; (c) a third $V_H$ CDR is identical to SEQ ID NO: 55; (d) a first $V_L$ CDR is identical to SEQ ID NO: 59; (e) a second $V_L$ CDR is identical to SEQ ID NO: 61; and (f) a third $V_L$ CDR is identical to SEQ ID NO: 63.

In particular aspects, the antibody comprises: (a) a first $V_H$ CDR is identical to SEQ ID NO: 3; (b) a second $V_H$ CDR is identical to SEQ ID NO: 5; (c) a third $V_H$ CDR is identical to SEQ ID NO: 7; (d) a first $V_L$ CDR is identical to SEQ ID NO: 11; (e) a second $V_L$ CDR is identical to SEQ ID NO: 13; and (f) a third $V_L$ CDR is identical to SEQ ID NO: 15. In particular aspects, the agonistic 4-1BB antibody comprises a $V_H$ domain at least about 80% (e.g., 81%, 82%, 83%, 84%, 85%, 86%, 87%, 88%, 89%, 90%, 91%, 92%, 93%, 94%, 95%, 96%, 97%, 98%, or 99%) identical to the $V_H$ domain of clone 54 (SEQ ID NO: 2) and a $V_L$ domain at least about 80% (e.g., 81%, 82%, 83%, 84%, 85%, 86%, 87%, 88%, 89%, 90%, 91%, 92%, 93%, 94%, 95%, 96%, 97%, 98%, or 99%) identical to the $V_L$ domain of clone 54 (SEQ ID NO: 10). In some aspects, the agonistic 4-1BB antibody comprises a $V_H$ domain identical to the $V_H$ domain of clone 54 (SEQ ID NO: 2) and a $V_L$ domain identical to the $V_L$ domain of clone 54 (SEQ ID NO: 10).

In certain aspects, the antibody comprises: (a) a first $V_H$ CDR is identical to SEQ ID NO: 19; (b) a second $V_H$ CDR is identical to SEQ ID NO: 21; (c) a third $V_H$ CDR is identical to SEQ ID NO: 23; (d) a first $V_L$ CDR is identical to SEQ ID NO: 27; (e) a second $V_L$ CDR is identical to SEQ ID NO: 29; and (f) a third $V_L$ CDR is identical to SEQ ID NO: 31. In some aspects, the antibody comprises a $V_H$ domain at least about 80% identical (e.g., 81%, 82%, 83%, 84%, 85%, 86%, 87%, 88%, 89%, 90%, 91%, 92%, 93%, 94%, 95%, 96%, 97%, 98%, or 99%) to the $V_H$ domain of clone 135B (SEQ ID NO: 18) and a $V_L$ domain at least about 80% (e.g., 81%, 82%, 83%, 84%, 85%, 86%, 87%, 88%, 89%, 90%, 91%, 92%, 93%, 94%, 95%, 96%, 97%, 98%, or 99%) identical to the $V_L$ domain of clone 135B (SEQ ID NO: 26). In particular aspects, the antibody comprises a $V_H$ domain identical to the $V_H$ domain of clone 135B (SEQ ID NO: 18) and a $V_L$ domain identical to the $V_L$ domain of clone 135B (SEQ ID NO: 26).

In some aspects, the antibody comprises: (a) a first $V_H$ CDR is identical to SEQ ID NO: 35; (b) a second $V_H$ CDR is identical to SEQ ID NO: 37; (c) a third $V_H$ CDR is identical to SEQ ID NO: 39; (d) a first $V_L$ CDR is identical to SEQ ID NO: 43; (e) a second $V_L$ CDR is identical to SEQ ID NO: 45; and (f) a third $V_L$ CDR is identical to SEQ ID NO: 47. In certain aspects, the antibody comprises a $V_H$ domain at least about 80% (e.g., 81%, 82%, 83%, 84%, 85%, 86%, 87%, 88%, 89%, 90%, 91%, 92%, 93%, 94%, 95%, 96%, 97%, 98%, or 99%) identical to the $V_H$ domain of clone 138 (SEQ ID NO: 34) and a $V_L$ domain at least about 80% (e.g., 81%, 82%, 83%, 84%, 85%, 86%, 87%, 88%, 89%, 90%, 91%, 92%, 93%, 94%, 95%, 96%, 97%, 98%, or 99%) identical to the $V_L$ domain of clone 138 (SEQ ID NO: 42). In specific aspects, the antibody comprises a $V_H$ domain identical to the $V_H$ domain of clone 138 (SEQ ID NO: 34) and a $V_L$ domain identical to the $V_L$ domain of clone 138 (SEQ ID NO: 42).

In certain aspects, the antibody comprises: (a) a first $V_H$ CDR is identical to SEQ ID NO: 51; (b) a second $V_H$ CDR is identical to SEQ ID NO: 53; (c) a third $V_H$ CDR is identical to SEQ ID NO: 55; (d) a first $V_L$ CDR is identical to SEQ ID NO: 59; (e) a second $V_L$ CDR is identical to SEQ ID NO: 61; and (f) a third $V_L$ CDR is identical to SEQ ID NO: 63. In some aspects, the antibody comprises a $V_H$ domain at least about 80% (e.g., 81%, 82%, 83%, 84%, 85%, 86%, 87%, 88%, 89%, 90%, 91%, 92%, 93%, 94%, 95%, 96%, 97%, 98%, or 99%) identical to the $V_H$ domain of clone 49A (SEQ ID NO: 50) and a $V_L$ domain at least about 80% (e.g., 81%, 82%, 83%, 84%, 85%, 86%, 87%, 88%, 89%, 90%, 91%, 92%, 93%, 94%, 95%, 96%, 97%, 98%, or 99%) identical to the $V_L$ domain of clone 49A (SEQ ID NO: 58). In certain aspects, the antibody comprises a $V_H$ domain identical to the $V_H$ domain of clone 49A (SEQ ID NO: 50) and a $V_L$ domain identical to the $V_L$ domain of clone 49A (SEQ ID NO: 58).

In some aspects, the agonistic 4-1BB antibody is recombinant. In certain aspects, the agonistic 4-1BB antibody is an IgG, IgM, IgA or an antigen binding fragment thereof. In some aspects, the agonistic 4-1BB antibody is a Fab', a F(ab')2, a F(ab')3, a monovalent scFv, a bivalent scFv, or a single domain antibody. In particular aspects, the agonistic 4-1BB antibody is a human, humanized antibody or de-immunized antibody.

In additional aspects, the method further comprises a resting step prior to step (b). In some aspects, the resting step comprises culturing the pre-activated T cells in the presence of IL-2. In particular aspects, the IL-2 is at a concentration of 6000 IU/mL. In some aspects, the resting step is performed for 2 days. In certain aspects, activating the pre-activated T cells comprises culturing in the presence of IL-2 and anti-CD3 antibody. In particular aspects, the anti-CD3 antibody is bound to a surface, such as a culture plate. For example, the culture plate is a 24-well culture plate.

In some aspects, genetically modifying comprises transducing the activated T cells with a viral construct. In certain aspects, the transducing is performed on a retronectin-coated surface. In some aspects, the viral construct is a retroviral vector. In some aspects, the viral construct encodes a chimeric antigen receptor (CAR) or T cell receptor (TCR). In particular aspects, the viral construct encodes a encodes a chemokine, cytokine, or costimulatory domain. In specific aspects, the chemokine is CXCR2. In some aspects, transducing is performed for 12-48 hours, such as 24 hours.

In certain aspects, expanding comprises culturing the genetically modified T cells in a bioreactor. In particular aspects, the bioreactor is a G-Rex 10 bioreactor.

In some aspects, the feeder cells are irradiated peripheral blood mononuclear cells (PBMCs). In particular aspects, the expanding is performed in the absence of anti-CD3 antibody. In some aspects, the IL-2 is at a concentration of 3000 IU/mL.

In certain aspects, media is exchanged once during the expanding step. In some aspects, expanding is performed for 10 to 16 days, such as 11, 12, 13, 14, 15, or 16 days. In particular aspects, expanding is performed for 14 days.

In some aspects, steps (a)-(d) are performed in 4-7 weeks, such as less than 6 weeks, less than 5 weeks, or 4 weeks. In particular aspects, at least 0.5 billion, such as 1, 10, 25, 50, 75, 100, 125, or 150 billion, expanded T cells are produced after step (d). In specific aspects, the method results in at least 500-fold, such as 750-, 1000-, 1500-, 2000-, 2500-, 3000-, 3500-, or 4000-fold, expansion from the starting population of T cells.

In certain aspects, the population of expanded T cells are CD8+ T cells or are enriched for CD8+ T cells compared to the cell population prior to expansion. In some aspects, the population of expanded T cells are CD4+ T cells or are enriched for CD4+ T cells compared to the cell population prior to expansion. In some aspects, the population of expanded T cells are GMP-compliant. The T cells may be allogeneic or autologous.

A further embodiment provides a pharmaceutical composition comprising a population of expanded T cells produced by the present embodiments and aspects thereof and a pharmaceutically acceptable carrier.

Another embodiment provides a composition comprising an effective amount of expanded T cells produced by the present embodiments and aspects thereof for use in the treatment of a disease or disorder in a subject.

In yet another embodiment, there is provided the use of a composition comprising an effective amount of expanded T cells produced by the present embodiments and aspects thereof for the treatment of an immune-related disorder in a subject.

A further embodiment provides a method for treating a disease or disorder comprising administering an effective amount of expanded T cells according to the present embodiments and aspects thereof to the subject.

In additional aspects, the method further comprises administering chemotherapy. In some aspects, the chemotherapy is administered prior to the expanded T cells. The chemotherapy may be myeloablative or non-myeloablative. In some aspects, the chemotherapy is lymphodepleting chemotherapy, such as fludarabine-based lymphodepleting chemotherapy. In some aspects, the chemotherapy is lenalidomide.

In particular aspects, the method does not comprise performing HLA matching. In some aspects, the disease or disorder is an immune-related disorder. In certain aspects, the immune-related disorder is an autoimmune disorder, graft versus host disease, allograft rejection, or inflammatory condition. In particular aspects, the disease or disorder is cancer.

In some aspects, the method further comprises administering at least a second therapeutic agent. In certain aspects, the at least a second therapeutic agent comprises chemotherapy, immunotherapy, surgery, radiotherapy, or biotherapy. In particular aspects, the T cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion. The T cells may be administered simultaneously with, prior to, or after the second therapeutic agent.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 2A) Multiple high-affinity anti-human 4-1BB antibodies were generated. Shown are ELISA results for initial post-fusion antibody supernatants against recombinant human 4-1BB. (FIGS. 2B-2C) Clone 54 4-1BB antibody (referred to herein as Curranlumab) amplifies human TIL with high efficiency. Two variants of clone 54 (Curranlumab) were used to amplify human tumor-infiltrating lymphocytes (TILs) from patient tumor chunks and the efficiency of each in generating pure, expanded CD8+ T cell products was compared to Urelumab (BMS-663513).

DESCRIPTION OF ILLUSTRATIVE EMBODIMENTS

Figure 1:
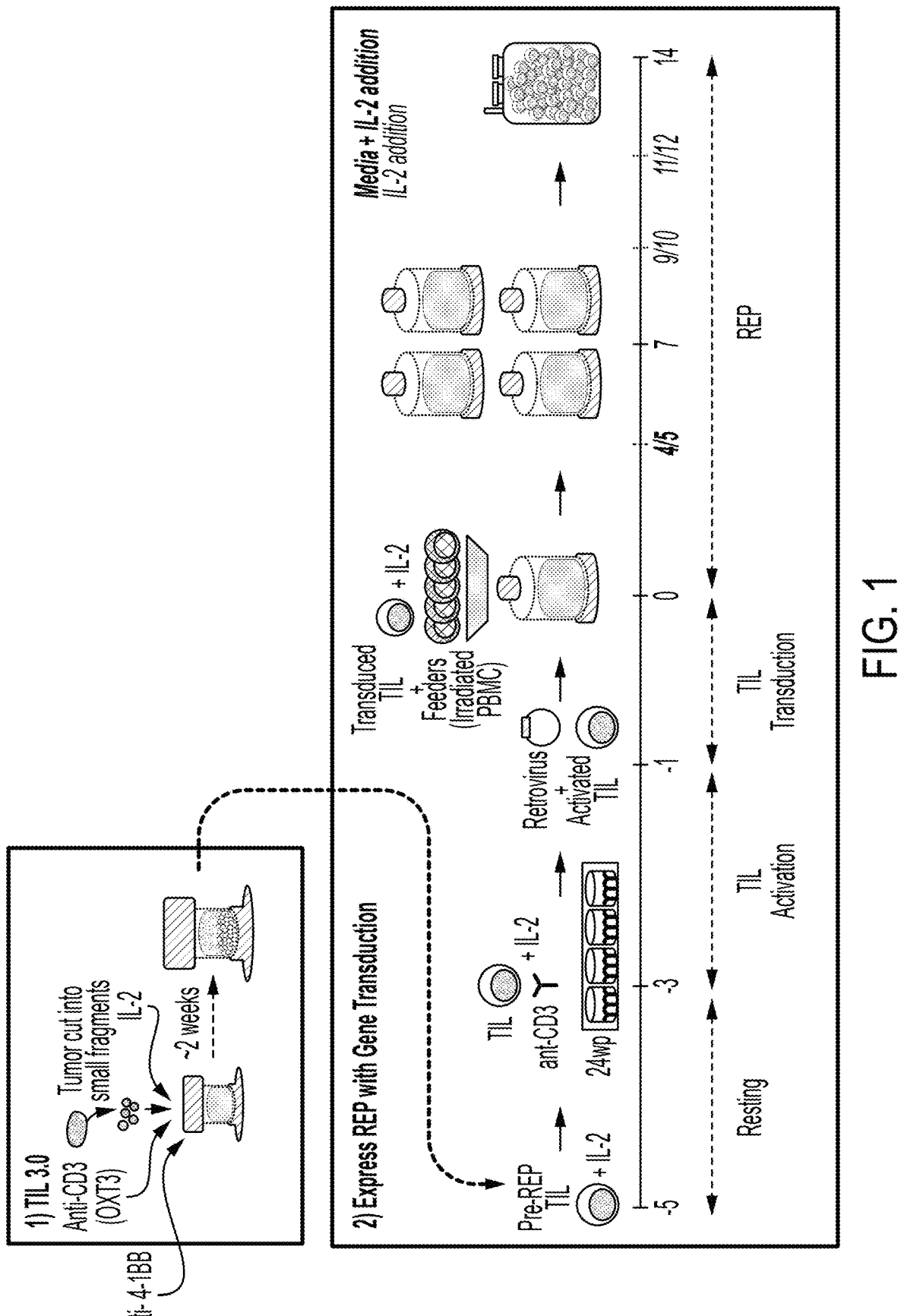
FIG. 1: Schematic depicting process of expanding tumor-infiltrating lymphocytes.

In certain embodiments, the present disclosure provides methods for expanding T cells from a starting population of T cells, such as TILs cultured from tumors. The method may comprise pre-activation of the starting population of T cells with an agonistic antibody, such as a 4-1BB (CD137) agonistic antibody in combination with an anti-CD3 (OKT3) antibody and IL-2. The pre-activated T cells may then be further activated in the presence of anti-CD3 antibody and IL-2. Next, the activated T cells can be genetically modified, such as by transduction with a viral vector. Finally, the genetically modified T cells may be expanded by express rapid expansion protocol (REP) in the presence of IL-2. The present methods may be used to generate genetically modified T cells with a high yield in a short period of time. In addition, the methods may be performed in a Good Manufacturing Practice (GMP) environment. Thus, the present methods can provide for efficient production of large numbers of GMP-grade, gene-modified TILs for the treatment of patients in a short period of time. The gene of interest may be a gene to increase the cytotoxicity, proliferation and/or persistence of T cells, such as a chemokine or cytokine. Exemplary genes include but are not limited to CXCR2 and the dominant negative form of TGF-βRII as well as CARs or TCRs.

In some embodiments, the 4-1BB agonistic antibody may be a human 4-1BB agonist antibody, particularly a 4-1BB IgG2a agonist monoclonal antibody. The 4-1BB antibody may be manufactured under GMP-compliant conditions. In specific aspects, the 4-1BB antibody is clone 54 4-1BB antibody, such as comprising CDRs 1-3 of the heavy chain of SEQ ID NO:2 (GYSFTDYN (SEQ ID NO:3), INPNYGTT (SEQ ID NO:5), and ARSPVEDYFDY (SEQ ID NO:7)) and the CDRs 1-3 of the light chain of SEQ ID NO:10 (SSVSSSY (SEQ ID NO:11), STS (SEQ ID NO:13), and QQYSGYPLIT (SEQ ID NO:15)). The anti-41BB antibody may have at least 80%, such as 85%, 90%, 91%, 92%, 93%, 94%, 95%, 96%, 97%, 98%, 99%, or 100%, sequence identity to SEQ ID NOs: 1, 2, 9, or 10.

In further embodiments, the present activated and expanded T cells may be used for the treatment of cancer patients, including but not limited to solid tumors. Manufacturing for any T cell therapy may include but is not limited to TILs, CAR T cells, or antigen-specific T cells derived from peripheral blood or other bodily fluids.

I. Definitions

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The term "about" means in general, the stated value plus or minus 5%.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of an antibody that activate 4-1BB signaling.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

The term "immune checkpoint" refers to a molecule such as a protein in the immune system which provides inhibitory signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR. The pathways involving LAGS, BTLA, B7H3, B7H4, TIM3, and KIR are recognized in the art to constitute immune checkpoint pathways similar to the CTLA-4 and PD-1 dependent pathways (see e.g. Pardoll, 2012; Mellman et al., 2011).

An "immune checkpoint inhibitor" refers to any compound inhibiting the function of an immune checkpoint protein. Inhibition includes reduction of function and full blockade. In particular the immune checkpoint protein is a human immune checkpoint protein. Thus, the immune checkpoint protein inhibitor in particular is an inhibitor of a human immune checkpoint protein.

The term "bioreactor" refers to a large-scale cell culture system that provides nutrients to cells and removes metabolites, as well as furnishes a physio-chemical environment conducive to cell growth, in a closed sterile system. In particular aspects, the biological and/or biochemical processes develop under monitored and controlled environmental and operating conditions, for example, pH, temperature, pressure, nutrient supply and waste removal.

II. Activation and Expansion of T Cells

In certain embodiments, the present disclosure provides methods for expanding T cells from a starting population of T cells, such as TILs cultured from tumors. The method may comprise pre-activation of the starting population of T cells with an agonistic antibody, such as a 4-1BB (CD137) agonistic antibody in combination with an anti-CD3 (OKT3) antibody and IL-2. The pre-activated T cells may then be further activated in the presence of anti-CD3 antibody and IL-2. Next, the activated T cells can be genetically modified, such as by transduction with a viral vector. Finally, the genetically modified T cells may be expanded by express rapid expansion protocol (REP) in the presence of IL-2.

A. Pre-Activation of T Cells

In some aspects, pre-activation of the starting population of T cells comprises culture with an anti-CD3 (OKT3) antibody for TCR stimulation, an agonistic 4-1BB antibody for co-stimulation, and high dose IL-2 for a three-signal approach for T cell activation. In particular embodiments, the present methods allow for the expansion of CD8 T cells at a high frequency in a shortened period of time. The anti-CD3 antibody may be a GMP-grade soluble antibody. The IL-2 may be human recombinant IL-2.

1. Starting Population of T Cells

In some embodiments, the T cells are derived from the blood, bone marrow, tumor tissue, lymph, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T (T$_N$) cells, effector T cells (T$_{EFF}$), memory T cells and sub-types thereof, such as stem cell memory T (TSC$_M$), central memory T (T$_{CM}$), effector memory T (T$_{EM}$), or terminally differentiated effector memory T (T$_{TEMRA}$) cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells). In one embodiment, the cells (e.g., CD8$^+$ cells or CD3$^+$ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, and/or IL7-Ra (CD127). In some examples, CD8$^+$ T cells are enriched for cells positive for CD45RO (or negative for CD45RA) and for CD62L.

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells from each other or to enrich CD4$^+$ or CD8$^+$ cell populations relative to the other. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ cells are further enriched for or depleted of naive, central memory, effector memory, and/or central memory stem cells, such as by positive or negative selection based on surface antigens associated with the respective subpopulation. In some embodiments, enrichment for central memory T (T$_{CM}$) cells is carried out to increase efficacy, such as to improve long-term survival, expansion, and/or engraftment following administration, which in some aspects is particularly robust in such subpopulations. In some embodiments, combining T$_{CM}$-enriched CD8$^+$ T cells and CD4$^+$ T cells further enhances efficacy.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about 2×10$^6$ lymphocytes), e.g., from about 5 to about 21 days.

The autologous T-cells can be modified to express a T-cell growth factor that promotes the growth and activation of the autologous T-cells. Suitable T-cell growth factors include, for example, interleukin (IL)-2, IL-7, IL-15, and IL-12. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. In particular aspects, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

In particular embodiments, TILs may be cultured from tumor fragments, such as a tumor samples obtained from a patient, such as a cancer patient. The tumor tissue may be cut into 1-3 mm$^3$ fragments, such as 2-40 fragments, specifically 5, 10, 20, or 30 fragments. In some aspects, 3, 4, or 5 fragments may be used in a bioreactor for the pre-activation step. The tumor fragments may be cultured in complete TIL media with IL-2 (e.g., 1-10,000 IU/mL, such as 2000, 3000, 4000, 5000, 6000, 7000, or 8000 IU/mL, particularly 6000 IU/mL) in 24-well plates for a period of 2-3 weeks. In particular aspects, the present methods have a shortened pre-activation period by culturing in the presence of three activation signals, including anti-41BB, anti-CD3, and IL-2. This culture period is shorted as compared to previous methods which comprise culture for 3-5 weeks.

2. Anti-41BB Antibodies

CD137 (4-1BB) is a member of the tumor necrosis receptor (TNF-R) gene family, which mediates cell proliferation, differentiation, and programmed cell death (apoptosis). The murine receptor was first characterized followed by the human homolog, which shares a 60% identity at the amino acid level, with significant conservation in the cytoplasmic/signaling domain. CD137 is mainly expressed in activated T-cells and NK cells, with varying levels detectable in thymocytes, myeloid cells, and endothelial cells at sites of inflammations. Physiological CD137 signaling is mediated via 1) NF-κB which promotes survival through Bcl-XL activation and 2) PI3K/ERK1/2 pathway which specifically drive cell cycle progression.

In certain embodiments, an antibody or a fragment thereof that binds to at least a portion of 4-1BB and activates signaling, such as to stimulate an immune response, is contemplated. As used herein, the term "antibody" is intended to refer broadly to any immunologic binding agent, such as IgG, IgM, IgA, IgD, IgE, and genetically modified IgG as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-41BB antibody is a monoclonal antibody or a humanized antibody.

In some embodiments, an anti-41BB antibody, an antigen-binding antibody fragment thereof, or VH and/or VL domains derived therefrom, can be generated using methods well known in the art and used in the present methods. In some embodiments, an anti-41BB antibody as described herein, an antigen-binding antibody fragment thereof, or VH and/or VL domains derived therefrom, may be used in the present methods. In some embodiments, a previously described anti-41BB antibody, an antigen-binding antibody fragment thereof, or VH and/or VL domains derived therefrom may be used in the present methods. In some embodiments, an anti-41BB antibody is selected from an antibody disclosed in any one of US Patent Application 2005/0095244; US Patent Application 2008/0166336 (such as ATCC Accession No. PTA-3885); US Patent Application 2020/0385479 (such as 20A12D11, 11E10D12, 23D2D6, 22F2C2, 30C11B4, 26B3D7); or PCT Application WO 2020/142624; the teachings of which are hereby incorporated by reference herein in their entirety. In some embodiments, an anti-41BB antibody is selected from an antibody disclosed in any one of U.S. Pat. Nos. 10,716,851; 8,821,867; 8,337,850; 7,288,638 (such as BMS-663513 and BMS-663031); 6,887,673 (BMS-554271); U.S. Pat. Nos. 7,214,493; 6,303,121; 6,569,997; 6,905,685; 6,355,476; 6,362,325 (such as BMS-469492 and BMS-469497); 6,974,863 (such as 53A2); 6,210,669 (such as 1D8, 3B8, or 3E1); U.S. Pat. Nos. 5,928,893; 6,303,121; or 6,569,997; the teachings of which are hereby incorporated by reference herein in their entirety. In some embodiments, the anti-41BB antibody may be selected from Urelumab (BMS-663513) or Utomilumab (PF-05082566). In some embodiments, the anti-41BB antibody may be Urelumab (BMS-663513).

In some embodiments, the anti-41BB antibody comprises CDRs 1-3 of the heavy chain of SEQ ID NO:2 (GYSFTDYN (SEQ ID NO:3), INPNYGTT (SEQ ID NO:5), and ARSPVEDYFDY (SEQ ID NO:7)) and the CDRs 1-3 of the light chain of SEQ ID NO:10 (SSVSSSY (SEQ ID NO:11), STS (SEQ ID NO:13), and QQYSGYPLIT (SEQ ID NO:15)). The anti-41BB antibody may have at least 80%, such as 85%, 90%, 91%, 92%, 93%, 94%, 95%, 96%, 97%, 98%, 99%, or 100%, sequence identity to SEQ ID NOs: 1, 2, 9, or 10. The anti-41BB antibody may have at least 80%, such as 85%, 90%, 91%, 92%, 93%, 94%, 95%, 96%, 97%, 98%, 99%, or 100%, sequence identity to SEQ ID NOs: 17, 18, 25, or 26. The anti-41BB antibody may have at least 80%, such as 85%, 90%, 91%, 92%, 93%, 94%, 95%, 96%, 97%, 98%, 99%, or 100%, sequence identity to SEQ ID NOs: 33, 34, 41, or 42. The anti-41BB antibody may have at least 80%, such as 85%, 90%, 91%, 92%, 93%, 94%, 95%, 96%, 97%, 98%, 99%, or 100%, sequence identity to SEQ ID NOs: 49, 50, 57, or 58. The heavy and light chain sequences are depicted below.

```
Clone 54 4-IBB VH Consensus Sequence starting from Frame 1 (FR1)(position 77- 505) IgG2a
Nucleotide sequence:
                                                                    (SEQ ID NO: 1)
GAGTTCCAGCTGCAGCAGTCTGGACCTGAGCTGGTGAAGCCTGGCGCTTCAGTGAA

GATATCCTGCAAGGCTTCTGGTTACTCATTCACTGACTACAACATGAACTGGGTGAA

GCAGAGCAATGGAAAGAGCCTTGAGTGGATTGGAGTAATTAATCCTAACTATGGTA

CTACTAGCTACAATCAGAAGTTCAAGGGCAAGGCCACATTTACTGTAGACCAATCTT

CCAGCACAGCCTACATGCAGCTCAACAGCCTGACATCTGAGGACTCTGCAGTCTATT

ACTGTGCAAGATCCCCGGTAGAGGACTACTTTGACTACTGGGGCCAAGGCACCACT

CTCACAGTCTCCTCAGCCAAAACAACAGCCCCATCGGTCTATCCACTGGCCCCTGTG

TGTGGAGGTACAACTGGCTCCTCGGTGACTCTA

Amino acid sequence:
                                                                    (SEQ ID NO: 2)
EFQLQQSGPELVKPGASVKISCKASGYSFTDYNMNWVKQSNGKSLEWIGVINPNYGTTS

YNQKFKGKATFTVDQSSSTAYMQLNSLTSEDSAVYYCARSPVEDYFDYWGQGTTLTVS

SAKTTAPSVYPLAPVCGGTTGSSVTL

CDR1:
                                                                    (SEQ ID NO: 3)
GYSFTDYN (SEQ ID NO: 4)
GGTTACTCATTCACTGACTACAAC

CDR2:
                                                                    (SEQ ID NO: 5)
INPNYGTT (SEQ ID NO: 6)
ATTAATCCTAACTATGGTACTACT

CDR3:
                                                                    (SEQ ID NO: 7)
ARSPVEDYFDY (SEQ ID NO: 8)
GCAAGATCCCCGGTAGAGGACTACTTTGACTAC

VL Consensus Sequence starting from Frame 1 (FR1) (position 91-470)
Nucleotide sequence:
                                                                    (SEQ ID NO: 9)
GAAAATGTGCTCACCCAGTCTCCAGCAATCATGTCTGCATCTCCAGGGGAAAAGGTC

ACCATGACCTGCAGGGCCAGGTCAAGTGTAAGTTCCAGTTACTTGCACTGGTACCAG
```

-continued

CAGAAGTCAGGTGCCTCCCCCAAACTCTGGATTTATAGCACATCCAACTTGGCTTCT

GGAGTCCCTGCTCGCTTCAGTGGCAGTGGGTCTGGGACCTCTTACTCTCTCACAATC

AGCAGTGTGGAGGCTGAAGATGCTGCCACTTATTACTGCCAGCAGTACAGTGGTTAC

CCACTCATCACGTTCGGTGCTGGGACCAAGCTGGA

GCTGAAACGGGCTGATGCTGCACCAACTGTATCCATCTTCCCACCATCCAGTGAGCA

GTT

Amino acid sequence:

(SEQ ID NO: 10)

ENVLTQSPAIMSASPGEKVTMTCRARSSVSSSYLHWYQQKSGASPKLWIYSTSNLASGV

PARFSGSGSGTSYSLTISSVEAEDAATYYCQQYSGYPLITFGAGTKLELKRADAAPTVSIF

PPSSEQ

CDR1:

(SEQ ID NO: 11)

SSVSSSY (SEQ ID NO: 12)

TCAAGTGTAAGTTCCAGTTAC

CDR2:

(SEQ ID NO: 13)

STS (SEQ ID NO: 14)

AGCACATCC
CDR3:

(SEQ ID NO: 15)

QQYSGYPLIT (SEQ ID NO: 16)

CAGCAGTACAGTGGTTACCCACTCATCACG

Clone 135B 4-1BB VH Consensus Sequence starting from Frame 1 (FR1)(position 45-407)
IgG1
Nucleotide sequence:

(SEQ ID NO: 17)

AGGTGAAGCTGCAGCAGTCAGGACCTGAGCTGGTGAAGCCTGGGGCTTCAGTGAAG

ATATCCTGTAAGGCTTCTGGATACACGTTCACTGACTACTACATGAACTGGGTGAAG

CAGAGCCATGGAAAGAGCCTTGAGTGGATTGGAGATATTAATCCTAACAATGATGG

TACTACCTACTACAACCAGAAGTTCAAGGGCAAGGCCACATTGACTGTAGACAAGT

CCTCCAGCACAGCCTACATGGAGCTCCGCAGCCTGACATCTGAGGACTCTGCAGTCT

ATTACTGTGCAAGATCCCTCTACGGTAGTAGCTACTACTTTGACTACTGGGGCCAAG

GCACCACTCTCACAGTCTCCTCAG

Amino acid sequence:

(SEQ ID NO: 18)

VKLQQSGPELVKPGASVKISCKASGYTFTDYYMNWVKQSHGKSLEWIGDINPNNDGTT

YYNQKFKGKATLTVDKSSSTAYMELRSLTSEDSAVYYCARSLYGSSYYFDYWGQGTTL

TVSS

CDR1:

(SEQ ID NO: 19)

GYTFTDYY (SEQ ID NO: 20)

GGATACACGTTCACTGACTACTAC

-continued

CDR2:

(SEQ ID NO: 21)

INPNNDGT (SEQ ID NO: 22)

ATTAATCCTAACAATGATGGTACT

CDR3:

(SEQ ID NO: 23)

ARSLYGSSYYFDY (SEQ ID NO: 24)

GCAAGATCCCTCTACGGTAGTAGCTACTACTTTGACTAC

VL Consensus Sequence starting from Frame 1 (FR1)(position 46-379)
Nucleotide sequence:

(SEQ ID NO: 25)

GATATTGTGATGACACAGTCTCCTGCTTCCTTAGCTGTATCTCTGGGGCAGAGGGCC

ACCATCTCATACAGGGCCAGCAAAAGTGTCAGTACATCTGGCTATAGTTATATGCAC

TGGAACCAACAGAAACCAGGACAGCCACCCAGACTCCTCATCTATCTTGTATCCAAC

CTAGAATCTGGGATCCCAGCCAGGTTTAGTGGCAGTGGGTCTGGGACAGACTTCACC

CTCAACATCCATCCTGTGGAGGAGGAGGATGCTGCAACCTATTACTGTCAGCAAAGT

AATGAGGACCCGTGGACGTTCGGTGGAGGCACCAAGCTGGAAATCAAAC

Amino acid sequence:

(SEQ ID NO: 26)

DIVMTQSPASLAVSLGQRATISYRASKSVSTSGYSYMHWNQQKPGQPPRLLIYLVSNLES

GIPARFSGSGSGTDFTLNIHPVEEEDAATYYCQQSNEDPWTFGGGTKLEIK

CDR1:

(SEQ ID NO: 27)

KSVSTSGYSY (SEQ ID NO: 28)

AAAAGTGTCAGTACATCTGGCTATAGTTAT

CDR2:

(SEQ ID NO: 29)

LVS (SEQ ID NO: 30)

CTTGTATCC

CDR3:

(SEQ ID NO: 31)

QQSNEDPWT (SEQ ID NO: 32)

CAGCAAAGTAATGAGGACCCGTGGACG

Clone 138 4-IBB VH Consensus Sequence starting from Frame 1 (FR1)(position 56-409)
IgG2b
Nucleotide sequence:

(SEQ ID NO: 33)

AGGTGCAGCTGCAGGAGTCTGGGGGAGGCTTAGTGAAGCCTGGAGGGTCCCTGAAA

CTCTCCTGTGCAGCCTCTGGATTCACTTTCAGTGACTATGGAATGCACTGGGTTCGTC

AGGCTCCAGAGAAGGGGCTGGAGTGGGTTGCATACATTAGTAGTGGCAGTAATTCC

ATCTACTATGCAGACACAGTGACGGGCCGATTCACCATCTCCAGAGACAATGCCAA

GAACACCCTGTTCCTGCAAATGACCAGTCTGAGGTCTGAGGACACGGCCATGTATTA

CTGTGCCTCGAATAATGGTTACTTCTACTTTGACTACTGGGGCCAAGGCACCACTCT

CACAGTCTCCTCAG

-continued

Amino acid sequence:

(SEQ ID NO: 34)

VQLQESGGGLVKPGGSLKLSCAASGFTFSDYGMHWVRQAPEKGLEWVAYISSGSNSIY

YADTVTGRFTISRDNAKNTLFLQMTSLRSEDTAMYYCASNNGYFYFDYWGQGTTLTVS

S

CDR1:

(SEQ ID NO: 35)

GFTFSTYG (SEQ ID NO: 36)

GGATTCACTTTCAGTGACTATGGA

CDR2:

(SEQ ID NO: 37)

ISSGSNSI (SEQ ID NO: 38)

ATTAGTAGTGGCAGTAATTCCATC

CDR3:

(SEQ ID NO: 39)

ASNNGYFYFDY (SEQ ID NO: 40)

GCCTCGAATAATGGTTACTTCTACTTTGACTAC

VL Consensus Sequence starting from Frame 1 (FR1)(position 63-378)
Nucleotide sequence:

(SEQ ID NO: 41)

ATTGTGATCACCCAGTCTCCAGCAATCCTGTCTGCATCTCCAGGGGAGAAGGTCACA

ATGACTTGCAGGGCCAGCTCAAGTGTAAGTTACATGCACTGGTACCAGCAGAAGCC

AGGATCCTCCCCCAAACCCTGGATTTATGCCACATCCAACCTGGCTTCTGGAGTCCC

TGCTCGCTTCAGTGGCAGTGGGTCTGGGACCTCTTACTCTCTCACAGTCAGCAGAGT

GGAGGCTGAAGATGCTGCCACTTATTACTGCCAGCAGTGGAGTAGTGACCCATTCAC

GTTCGGCTCGGGGACAAAGTTGGAAATAAAAC

Amino acid sequence:

(SEQ ID NO: 42)

IVITQSPAILSASPGEKVTMTCRASSSVSYMHWYQQKPGSSPKPWIYATSNLASGVPARF

SGSGSGTSYSLTVSRVEAEDAATYYCQQWSSDPFTFGSGTKLEIK

CDR1:

(SEQ ID NO: 43)

SSVSY (SEQ ID NO: 44)

TCAAGTGTAAGTTAC

CDR2:

(SEQ ID NO: 45)

ATS (SEQ ID NO: 46)

GCCACATCC

CDR3:

(SEQ ID NO: 47)

QQWSSDPFT (SEQ ID NO: 48)

CAGCAGTGGAGTAGTGACCCATTCACG

Clone 49A 4-IBB VH Consensus Sequence starting from Frame 1 (FR1)(position 65-427) IgG1
Nucleotide sequence:

(SEQ ID NO: 49)

AGGTGAAACTGCAGCAGTCAGGACCTGAGCTGGTGAAGCCTGGGGCTTCAGTGAAG

ATATCCTGTAAGGCTTCTGGATACACGTTCACTGACTACTACATGAACTGGGTGAAG

GAGAGCCATGGAAAGAGCCTTGAGTGGATTGGAGATATTAATCCTAACAATGGTGG

-continued

TTCTACCTACTACAACCAGAAGTTCAAGGGCAAGGCCACATTGACTGTAGAGAAGT

CCTCCAGCACAGCCTTCATGGAGCTCCGCAGCCTGACATCTGAGGACTCTGCAGTCT

ATTACTGTGCAAGATCCCTCTACGGTAGTACCTACTACTTTGACTACTGGGGCCAAG

GCACCCCTCTCACAGTCTCCTCAG

Amino acid sequence:

(SEQ ID NO: 50)

VKLQQSGPELVKPGASVKISCKASGYTFTDYYMNWVKESHGKSLEWIGDINPNNGGST

YYNQKFKGKATLTVEKSSSTAFMELRSLTSEDSAVYYCARSLYGSTYYFDYWGQGTPL

TVSS

CDR1:

(SEQ ID NO: 51)

GYTFTDYY (SEQ ID NO: 52)

GGATACACGTTCACTGACTACTAC

CDR2:

(SEQ ID NO: 53)

INPNNGGS (SEQ ID NO: 54)

ATTAATCCTAACAATGGTGGTTCT

CDR3:

(SEQ ID NO: 55)

ARSLYGSTYYFDY (SEQ ID NO: 56)

GCAAGATCCCTCTACGGTAGTACCTACTACTTTGACTAC

VL Consensus Sequence starting from Frame 1 (FR1)(position 55-388)
Nucleotide sequence:

(SEQ ID NO: 57)

GATATTGTGCTGACCCAGTCTCCAGCTTCTTTGGCTGTGTCTCTAGGGCAGAGGGCC

ACCATCTCCTGCAAGGCCAGCCAAAGTGTTGATTATGATGGTGATAGTTATATGAAC

TGGTACCAACAGAAGCCAGGACAGCCACCCAAACTCCTCATCTATGCTGCATCCAAT

CTAGAATCTGGGATCCCAGCCAGGTTTAGTGGCAGTGGGTCTGGGACAGACTTCACT

CTCAACATCCATCCTGTGGAGGAGGAGGATGCTGGAACCTATTACTGTCAGCAAAGT

AATGACGATCCGTGGACGTTCGGTGGAGGCACCAAGCTGGAAATCAAAC

Amino acid sequence:

(SEQ ID NO: 58)

DIVLTQSPASLAVSLGQRATISCKASQSVDYDGDSYMNWYQQKPGQPPKLLIYAASNLE

SGIPARFSGSGSGTDFTLNIHPVEEEDAGTYYCQQSNDDPWTFGGGTKLEIK

CDR1:

(SEQ ID NO: 59)

QSVDYDGDSY (SEQ ID NO: 60)

CAAAGTGTTGATTATGATGGTGATAGTTAT

CDR2:

(SEQ ID NO: 61)

AAS (SEQ ID NO: 62)

GCTGCATCC

CDR3:

(SEQ ID NO: 63)

QQSNDDPWT (SEQ ID NO: 64)

CAGCAAAGTAATGACGATCCGTGGACG

Thus, by known means and as described herein, polyclonal or monoclonal antibodies, antibody fragments, and binding domains and CDRs (including engineered forms of any of the foregoing) may be created that are specific to 4-1BB, one or more of its respective 35 epitopes, or conjugates of any of the foregoing, whether such antigens or epitopes are isolated from natural sources or are synthetic derivatives or variants of the natural compounds.

Examples of antibody fragments suitable for the present embodiments include, without limitation: (i) the Fab fragment, consisting of $V_L$, $V_H$, $C_L$, and $C_{H1}$ domains; (ii) the "Fd" fragment consisting of the $V_H$ and $C_{H1}$ domains; (iii) the "Fv" fragment consisting of the $V_L$ and $V_H$ domains of a single antibody; (iv) the "dAb" fragment, which consists of a $V_H$ domain; (v) isolated CDR regions; (vi) F(ab')2 fragments, a bivalent fragment comprising two linked Fab fragments; (vii) single chain Fv molecules ("scFv"), wherein a $V_H$ domain and a $V_L$ domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the $V_H$ and $V_L$ domains. Minibodies comprising a scFv joined to a CH3 domain may also be made.

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as a 4-1BB extracellular domain (ECD) protein, in order to produce antibodies specific for 4-1BB. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a 4-1BB antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

Plasma B cells (CD45$^+$CD5$^-$CD19$^+$) may be isolated from freshly prepared rabbit peripheral blood mononuclear cells of immunized rabbits and further selected for 4-1BB binding cells. After enrichment of antibody producing B cells, total RNA may be isolated and cDNA synthesized. DNA sequences of antibody variable regions from both heavy chains and light chains may be amplified, constructed into a phage display Fab expression vector, and transformed into *E. coli*. 4-1BB specific binding Fab may be selected out through multiple rounds enrichment panning and sequenced. Selected 4-1BB binding hits may be expressed as full-length IgG in rabbit and rabbit/human chimeric forms using a mammalian expression vector system in human embryonic kidney (HEK293) cells (Invitrogen) and purified using a protein G resin with a fast protein liquid chromatography (FPLC) separation unit.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881, 557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/0172677; and U.S. Pat. Nos. 3,817,837; 3,850,752; 3,939, 350; 3,996,345; 4,196,265; 4,275,149; 4,277,437; 4,366, 241; 4,469,797; 4,472,509; 4,606,855; 4,703,003; 4,742, 159; 4,767,720; 4,816,567; 4,867,973; 4,938,948; 4,946, 778; 5,021,236; 5,164,296; 5,196,066; 5,223,409; 5,403, 484; 5,420,253; 5,565,332; 5,571,698; 5,627,052; 5,656, 434; 5,770,376; 5,789,208; 5,821,337; 5,844,091; 5,858, 657; 5,861,155; 5,871,907; 5,969,108; 6,054,297; 6,165, 464; 6,365,157; 6,406,867; 6,709,659; 6,709,873; 6,753, 407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946, 546, which is incorporated herein by reference.

It is fully expected that antibodies to 4-1BB will have the ability to neutralize or counteract the effects of 4-1BB regardless of the animal species, monoclonal cell line, or other source of the antibody. Certain animal species may be less preferable for generating therapeutic antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% may be an antibody that binds 4-1BB.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against 4-1BB, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radio-labels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

B. Bioreactor

The present method may comprise culture in a functionally closed system, such as a bioreactor. One or more culture steps, such as the pre-activation and express REP steps, may be performed in the bioreactor. In particular aspects, the whole T cell expansion method is performed in a bioreactor. Activation and/or expansion may be performed in a gas-permeable bioreactor, such as G-Rex cell culture device. The bioreactor may support between $1 \times 10^9$ and $6 \times 10^9$ total cells in an average 1000 mL volume.

Bioreactors can be grouped according to general categories including: static bioreactors, stirred flask bioreactors, rotating wall vessel bioreactors, hollow fiber bioreactors and direct perfusion bioreactors. Within the bioreactors, cells can be free, or immobilized, seeded on porous 3-dimensional scaffolds (hydrogel).

Hollow fiber bioreactors can be used to enhance the mass transfer during culture. A Hollow fiber bioreactor is a 3D cell culturing system based on hollow fibers, which are small, semi-permeable capillary membranes arranged in parallel array with a typical molecular weight cut-off (MWCO) range of 10-30 kDa. These hollow fiber membranes are often bundled and housed within tubular polycarbonate shells to create hollow fiber bioreactor cartridges. Within the cartridges, which are also fitted with inlet and outlet ports, are two compartments: the intracapillary (IC) space within the hollow fibers, and the extracapillary (EC) space surrounding the hollow fibers.

Thus, for the present disclosure, the bioreactor may be a hollow fiber bioreactor. Hollow fiber bioreactors may have the cells embedded within the lumen of the fibers, with the medium perfusing the extra-lumenal space or, alternatively, may provide gas and medium perfusion through the hollow fibers, with the cells growing within the extralumenal space.

The hollow fibers should be suitable for the delivery of nutrients and removal of waste in the bioreactor. The hollow fibers may be any shape, for example, they may be round and tubular or in the form of concentric rings. The hollow fibers may be made up of a resorbable or non-resorbable membrane. For example, suitable components of the hollow fibers include polydioxanone, polylactide, polyglactin, polyglycolic acid, polylactic acid, polyglycolic acid/trimethylene carbonate, cellulose, methylcellulose, cellulosic polymers, cellulose ester, regenerated cellulose, pluronic, collagen, elastin, and mixtures thereof.

The bioreactor may be primed prior to seeding of the cells. The priming may comprise flushing with a buffer, such as PBS. The bioreactor may then be washed with media.

In specific embodiments, the present methods use a GRex bioreactor. The base of the GRex flask is a gas permeable membrane on which cells reside. Hence, cells are in a highly oxygenated environment, allowing them to be grown to high densities. The system scales up easily and requires less frequent culture manipulations. GRex flasks are compatible with standard tissue culture incubators and cellular laboratory equipment, reducing the specialized equipment and capital investment required to initiate an ACT program.

The TIL may be seeded in the bioreactor for Rapid Expansion at a density of about 4000-10000 cells/cm$^2$, such as about 4000 cells/cm$^2$, about 4500 cells/cm$^2$, about 5000 cells/cm$^2$, about 5500 cells/cm$^2$, such as about 6000 cells/cm$^2$, such as about 6500 cells/cm$^2$, such as about 7000 cells/cm$^2$, such as about 7500 cells/cm$^2$, such as about 8000 cells/cm$^2$, such as about 8500 cells/cm$^2$, such as about 9000 cells/cm$^2$, such as about 9500 cells/cm$^2$, such as about 10000 cells/cm$^2$. Particularly, the cells may be seeded at a cell density of about 4000-6000 cells/cm$^2$, such as about 5000 cells/cm$^2$.

The total number of cells seeded in the bioreactor, such as the G-Rex with 100 cm square flasks, may be about $4.0\times10^6$ to about $4.0\times10^8$ cells, such as about $1.0\times10^6$ to $5.0.0\times10^6$, $5.0\times10^6$ to $1.0\times10^7$, $1.0\times10^7$ to $5.0\times10^7$, $5.0\times10^7$ to $1.0\times10^8$ cells. In particular aspects, the total number of cells seeded in the bioreactor are about $1.0\times10^7$ to about $3.0\times10^7$, such as about $2.0\times10^7$ cells. The seeding cell density at day 0 may be low while the sub-cultured cells at day 7 may be seeded at a higher density. The cell density may be adjusted based on the size of the bioreactor selected for the expansion.

The cells may be seeded in any suitable cell culture media, many of which are commercially available. Exemplary media include DMEM, RPMI, MEM, Media 199, HAMS and the like. The media may be supplemented with one or more of the following: growth factors, cytokines, hormones, or B27, antibiotics, vitamins and/or small molecule drugs. Particularly, the media may be serum-free.

In some embodiments the cells may be incubated at room temperature. The incubator may be humidified and have an atmosphere that is about 5% $CO_2$ and about 1% $O_2$. In some embodiments, the $CO_2$ concentration may range from about 1-20%, 2-10%, or 3-5%. In some embodiments, the $O_2$ concentration may range from about 1-20%, 2-10%, or 3-5%.

C. T Cell Activation

After pre-activation, the T cells may undergo a resting period in complete TIL medium with IL-2, such as 6000 IU/mL IL-2, for a period of 24-72 hours (e.g., 1, 2, or 3 days), such as at a concentration of $1.5\times10^6$/mL.

After the resting period, the cells may be activated in the presence of IL-2 and anti-CD3. In particular aspects, the culture is in a multi-well plate, such as a 6-well, 24-well, or 48-well plate. The culture plate may be coated with anti-CD3 at a concentration of 1-1,000 ng/mL, such as 3, 10, 30, 100, 300, or 1,000 ng/mL, particularly at 300 ng/mL. The cells may be activated for 24-72 hours (e.g., 1, 2, or 3 days) in the presence of 6000 IU/mL IL-2 at 37° C. and 5% $CO_2$ to produce activated T cells, such as activated TILs.

D. Genetic Modification of Activated T Cells

The activated T cells may then be genetically modified, such as to express a gene of interest or an antigen receptor. In some embodiments, the activated T-cells can be genetically modified to express an antigen receptor such as chimeric antigen receptor or T cell receptor, an antigen, such as a tumor antigen, or a T-cell growth factor that promotes the growth and activation of the autologous T-cells. In some embodiments, the cells are genetically engineered by a viral supernatant. For example, the cells may be transduced on a retronectin-coated plate which is blocked, such as with 2.5% human serum albumin for 20 minutes to an hour. Viral vector supernatant may then be added to the plates which are then centrifuged, such as at 2,000 g for 2 hours at 32° C. The supernatant may then be removed from the plates and the activated T cells may be added to the plates, such as at a concentration of 0.8 to $1.2\times10^6$/mL. The plates can then be centrifuged, such as at 1,000 g for 10 min, and incubated at standard conditions overnight until the initiation of REP. In other embodiments, the cells may be genetically engineered by non-viral methods, such as transposon-based systems including CRISPR or sleeping beauty.

1. Antigen Receptors

The T cells of the present disclosure can be genetically engineered to express antigen receptors such as engineered TCRs or CARs. For example, the T cells are modified to express a TCR having antigenic specificity for a cancer antigen.

Suitable methods of modification are known in the art. See, for instance, Sambrook and Ausubel, supra. For example, the cells may be transduced to express a TCR having antigenic specificity for a cancer antigen using transduction techniques described in Heemskerk et al., 2008 and Johnson et al., 2009.

Electroporation of RNA coding for the full length TCR α and β (or γ and δ) chains can be used as alternative to overcome long-term problems with autoreactivity caused by pairing of retrovirally transduced and endogenous TCR chains. Even if such alternative pairing takes place in the transient transfection strategy, the possibly generated autoreactive T cells will lose this autoreactivity after some time, because the introduced TCR α and β chain are only transiently expressed. When the introduced TCR α and β chain expression is diminished, only normal autologous T cells are left. This is not the case when full length TCR chains are introduced by stable retroviral transduction, which will never lose the introduced TCR chains, causing a constantly present autoreactivity in the patient.

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., 2012; Wu et al., 2012. In some aspects, the genetically engineered antigen receptors include a CAR as described in U.S. Pat. No. 7,446,190, and those described in International Patent Application Publication No.: WO/2014055668 A1.

a. Chimeric Antigen Receptors

In some embodiments, the CAR comprises: a) an intracellular signaling domain, b) a transmembrane domain, and c) an extracellular domain comprising an antigen binding region.

In some embodiments, the engineered antigen receptors include CARs, including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, DAP12, and 4-1BB (CD137).

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In certain embodiments of the chimeric antigen receptor, the antigen-specific portion of the receptor (which may be referred to as an extracellular domain comprising an antigen binding region) comprises a tumor associated antigen or a pathogen-specific antigen binding domain. Antigens include carbohydrate antigens recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR may be co-expressed with a cytokine to improve persistence when there is a low amount of tumor-associated antigen. For example, CAR may be co-expressed with IL-15.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

b. T Cell Receptor (TCR)

In some embodiments, the genetically engineered antigen receptors include recombinant TCRs and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form.

Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable a chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3– and ζ-chains, together with the TCR, form what is known as the T cell receptor complex.

In some embodiments, the TCR may be a heterodimer of two chains a and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T cell hybridomas or other publicly available source. In some embodiments, the T cells can be obtained from in vivo isolated cells. In some embodiments, a high-affinity T cell clone can be isolated from a patient, and the TCR isolated. In some embodiments, the T cells can be a cultured T cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005). In some embodiments, the TCR or antigen-binding portion thereof can be synthetically generated from knowledge of the sequence of the TCR.

c. Antigens

Among the antigens targeted by the genetically engineered antigen receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

Any suitable antigen may find use in the present method. Exemplary antigens include, but are not limited to, antigenic molecules from infectious agents, auto-/self-antigens, tumor-/cancer-associated antigens, and tumor neoantigens. In particular aspects, the antigens include NY-ESO, EGFRvIII, Muc-1, Her2, CA-125, WT-1, Mage-A3, Mage-A4, Mage-A10, TRAIL/DR4, and CEA. In particular aspects, the antigens for the two or more antigen receptors include, but are not limited to, CD19, EBNA, WT1, CD123, NY-ESO, EGFRvIII, MUC1, HER2, CA-125, WT1, Mage-A3, Mage-A4, Mage-A10, TRAIL/DR4, and/or CEA. The sequences for these antigens are known in the art, for example, CD19 (Accession No. NG_007275.1), EBNA (Accession No. NG_002392.2), WT1 (Accession No. NG_009272.1), CD123 (Accession No. NC_000023.11), NY-ESO (Accession No. NC_000023.11), EGFRvIII (Accession No. NG_007726.3), MUC1 (Accession No. NG_029383.1), HER2 (Accession No. NG_007503.1), CA-125 (Accession No. NG_055257.1), WT1 (Accession No. NG_009272.1), Mage-A3 (Accession No. NG_013244.1), Mage-A4 (Accession No. NG_013245.1), Mage-A10 (Accession No. NC_000023.11), TRAIL/DR4 (Accession No. NC_000003.12), and/or CEA (Accession No. NC_000019.10).

Tumor-associated antigens may be derived from prostate, breast, colorectal, lung, pancreatic, renal, mesothelioma, ovarian, sarcoma or melanoma cancers. Exemplary tumor-associated antigens or tumor cell-derived antigens include MAGE 1, 3, and MAGE 4 (or other MAGE antigens such as those disclosed in International Patent Publication No. WO99/40188); PRAME; BAGE; RAGE, Lage (also known as NY ESO 1); SAGE; and HAGE or GAGE. These non-limiting examples of tumor antigens are expressed in a wide range of tumor types such as melanoma, lung carcinoma, sarcoma, and bladder carcinoma. See, e.g., U.S. Pat. No. 6,544,518. Prostate cancer tumor-associated antigens include, for example, prostate specific membrane antigen (PSMA), prostate-specific antigen (PSA), prostatic acid phosphates, NKX3.1, and six-transmembrane epithelial antigen of the prostate (STEAP).

Other tumor associated antigens include Plu-1, HASH-1, HasH-2, Cripto and Criptin. Additionally, a tumor antigen may be a self peptide hormone, such as whole length gonadotrophin hormone releasing hormone (GnRH), a short 10 amino acid long peptide, useful in the treatment of many cancers.

Tumor antigens include tumor antigens derived from cancers that are characterized by tumor-associated antigen expression, such as HER-2/neu expression. Tumor-associated antigens of interest include lineage-specific tumor antigens such as the melanocyte-melanoma lineage antigens MART-1/Melan-A, gp100, gp75, mda-7, tyrosinase and tyrosinase-related protein. Illustrative tumor-associated antigens include, but are not limited to, tumor antigens derived from or comprising any one or more of, p53, Ras, c-Myc, cytoplasmic serine/threonine kinases (e.g., A-Raf, B-Raf, and C-Raf, cyclin-dependent kinases), MAGE-A1, MAGE-A2, MAGE-A3, MAGE-A4, MAGE-A6, MAGE-A10, MAGE-A12, MART-1, BAGE, DAM-6, -10, GAGE-1, -2, -8, GAGE-3, -4, -5, -6, -7B, NA88-A, MART-1, MC1R, Gp100, PSA, PSM, Tyrosinase, TRP-1, TRP-2, ART-4, CAMEL, CEA, Cyp-B, hTERT, hTRT, iCE, MUC1, MUC2, Phosphoinositide 3-kinases (PI3Ks), TRK receptors, PRAME, P15, RU1, RU2, SART-1, SART-3, Wilms' tumor antigen (WT1), AFP, -catenin/m, Caspase-8/m, CEA, CDK-4/m, ELF2M, GnT-V, G250, HSP70-2M, HST-2, KIAA0205, MUM-1, MUM-2, MUM-3, Myosin/m, RAGE, SART-2, TRP-2/INT2, 707-AP, Annexin II, CDC27/m, TPI/mbcr-abl, BCR-ABL, interferon regulatory factor 4 (IRF4), ETV6/AML, LDLR/FUT, Pml/RAR, Tumor-associated calcium signal transducer 1 (TACSTD1) TACSTD2, receptor tyrosine kinases (e.g., Epidermal Growth Factor receptor (EGFR) (in particular, EGFRvIII), platelet derived growth factor receptor (PDGFR), vascular endothelial growth factor receptor (VEGFR)), cytoplasmic tyrosine kinases (e.g., src-family, syk-ZAP70 family), integrin-linked kinase (ILK), signal transducers and activators of transcription STATS, STATS, and STATE, hypoxia inducible factors (e.g., HIF-1 and HIF-2), Nuclear Factor-Kappa B (NF-B), Notch receptors (e.g., Notch1-4), c-Met, mammalian targets of rapamycin (mTOR), WNT, extracellular signal-regulated kinases (ERKs), and their regulatory subunits, PMSA, PR-3, MDM2, Mesothelin, renal cell carcinoma-5T4, SM22-alpha, carbonic anhydrases I (CAI) and IX (CAIX) (also known as G250), STEAD, TEL/AML1, GD2, proteinase3, hTERT, sarcoma translocation breakpoints, EphA2, ML-IAP, EpCAM, ERG (TMPRSS2 ETS fusion gene), NA17, PAX3, ALK, androgen receptor, cyclin B1, polysialic acid, MYCN, RhoC, GD3, fucosyl GM1, mesothelian, PSCA, sLe, PLAC1, GM3, BORIS, Tn, GLoboH, NY-BR-1, RGsS, SART3, STn, PAXS, OY-TES1, sperm protein 17, LCK, HMWMAA, AKAP-4, SSX2, XAGE 1, B7H3, legumain, TIE2, Page4, MAD-CT-1, FAP, MAD-CT-2, fos related antigen 1, CBX2, CLDN6, SPANX, TPTE, ACTL8, ANKRD30A, CDKN2A, MAD2L1, CTAG1B, SUNC1, LRRN1 and idiotype.

Antigens may include epitopic regions or epitopic peptides derived from genes mutated in tumor cells or from genes transcribed at different levels in tumor cells compared to normal cells, such as telomerase enzyme, survivin, mesothelin, mutated ras, bcr/abl rearrangement, Her2/neu, mutated or wild-type p53, cytochrome P450 1B1, and abnormally expressed intron sequences such as N-acetylglucosaminyltransferase-V; clonal rearrangements of immunoglobulin genes generating unique idiotypes in myeloma and B-cell lymphomas; tumor antigens that include epitopic regions or epitopic peptides derived from oncoviral processes, such as human papilloma virus proteins E6 and E7; Epstein bar virus protein LMP2; nonmutated oncofetal proteins with a tumor-selective expression, such as carcinoembryonic antigen and alpha-fetoprotein.

In other embodiments, an antigen is obtained or derived from a pathogenic microorganism or from an opportunistic pathogenic microorganism (also called herein an infectious disease microorganism), such as a virus, fungus, parasite, and bacterium. In certain embodiments, antigens derived from such a microorganism include full-length proteins.

Illustrative pathogenic organisms whose antigens are contemplated for use in the method described herein include human immunodeficiency virus (HIV), herpes simplex virus (HSV), respiratory syncytial virus (RSV), cytomegalovirus (CMV), Epstein-Barr virus (EBV), Influenza A, B, and C, vesicular stomatitis virus (VSV), vesicular stomatitis virus (VSV), polyomavirus (e.g., BK virus and JC virus), adenovirus, Staphylococcus species including Methicillin-resistant Staphylococcus aureus (MRSA), and Streptococcus species including Streptococcus pneumoniae. As would be understood by the skilled person, proteins derived from these and other pathogenic microorganisms for use as antigen as described herein and nucleotide sequences encoding the proteins may be identified in publications and in public databases such as GENBANK®, SWISS-PROT®, and TREMBL®.

Antigens derived from human immunodeficiency virus (HIV) include any of the HIV virion structural proteins (e.g., gp120, gp41, p17, p24), protease, reverse transcriptase, or HIV proteins encoded by tat, rev, nef, vif, vpr and vpu.

Antigens derived from herpes simplex virus (e.g., HSV 1 and HSV2) include, but are not limited to, proteins expressed from HSV late genes. The late group of genes predominantly encodes proteins that form the virion particle. Such proteins include the five proteins from (UL) which form the viral capsid: UL6, UL18, UL35, UL38 and the major capsid protein UL19, UL45, and UL27, each of which may be used as an antigen as described herein. Other illustrative HSV proteins contemplated for use as antigens herein include the ICP27 (H1, H2), glycoprotein B (gB) and glycoprotein D (gD) proteins. The HSV genome comprises at least 74 genes, each encoding a protein that could potentially be used as an antigen.

Antigens derived from cytomegalovirus (CMV) include CMV structural proteins, viral antigens expressed during the immediate early and early phases of virus replication, glycoproteins I and III, capsid protein, coat protein, lower matrix protein pp65 (ppUL83), p52 (ppUL44), IE1 and 1E2 (UL123 and UL122), protein products from the cluster of genes from UL128-UL150, envelope glycoprotein B (gB), gH, gN, and pp150. As would be understood by the skilled person, CMV proteins for use as antigens described herein may be identified in public databases such as GENBANK®, SWISS-PROT®, and TREMBL®.

Antigens derived from Epstein-Ban virus (EBV) that are contemplated for use in certain embodiments include EBV lytic proteins gp350 and gp110, EBV proteins produced during latent cycle infection including Epstein-Ban nuclear antigen (EBNA)-1, EBNA-2, EBNA-3A, EBNA-3B, EBNA-3C, EBNA-leader protein (EBNA-LP) and latent membrane proteins (LMP)-1, LMP-2A and LMP-2B.

Antigens derived from respiratory syncytial virus (RSV) that are contemplated for use herein include any of the eleven proteins encoded by the RSV genome, or antigenic fragments thereof: NS 1, NS2, N (nucleocapsid protein), M (Matrix protein) SH, G and F (viral coat proteins), M2 (second matrix protein), M2-1 (elongation factor), M2-2 (transcription regulation), RNA polymerase, and phosphoprotein P.

Antigens derived from Vesicular stomatitis virus (VSV) that are contemplated for use include any one of the five major proteins encoded by the VSV genome, and antigenic fragments thereof: large protein (L), glycoprotein (G), nucleoprotein (N), phosphoprotein (P), and matrix protein (M).

Antigens derived from an influenza virus that are contemplated for use in certain embodiments include hemagglutinin (HA), neuraminidase (NA), nucleoprotein (NP), matrix proteins M1 and M2, NS1, NS2 (NEP), PA, PB1, PB1-F2, and PB2.

Exemplary viral antigens also include, but are not limited to, adenovirus polypeptides, alphavirus polypeptides, calicivirus polypeptides (e.g., a calicivirus capsid antigen), coronavirus polypeptides, distemper virus polypeptides, Ebola virus polypeptides, enterovirus polypeptides, flavivirus polypeptides, hepatitis virus (AE) polypeptides (a hepatitis B core or surface antigen, a hepatitis C virus E1 or E2 glycoproteins, core, or non-structural proteins), herpesvirus polypeptides (including a herpes simplex virus or varicella zoster virus glycoprotein), infectious peritonitis virus polypeptides, leukemia virus polypeptides, Marburg virus polypeptides, orthomyxovirus polypeptides, papilloma virus polypeptides, parainfluenza virus polypeptides (e.g., the hemagglutinin and neuraminidase polypeptides), paramyxovirus polypeptides, parvovirus polypeptides, pestivirus polypeptides, picorna virus polypeptides (e.g., a poliovirus capsid polypeptide), pox virus polypeptides (e.g., a vaccinia virus polypeptide), rabies virus polypeptides (e.g., a rabies virus glycoprotein G), reovirus polypeptides, retrovirus polypeptides, and rotavirus polypeptides.

In certain embodiments, the antigen may be bacterial antigens. In certain embodiments, a bacterial antigen of interest may be a secreted polypeptide. In other certain embodiments, bacterial antigens include antigens that have a portion or portions of the polypeptide exposed on the outer cell surface of the bacteria.

Antigens derived from *Staphylococcus* species including Methicillin-resistant *Staphylococcus aureus* (MRSA) that are contemplated for use include virulence regulators, such as the Agr system, Sar and Sae, the Arl system, Sar homologues (Rot, MgrA, SarS, SarR, SarT, SarU, SarV, SarX, SarZ and TcaR), the Srr system and TRAP. Other *Staphylococcus* proteins that may serve as antigens include Clp proteins, HtrA, MsrR, aconitase, CcpA, SvrA, Msa, CfvA and CfvB (see, e.g., *Staphylococcus*: Molecular Genetics, 2008 Caister Academic Press, Ed. Jodi Lindsay). The genomes for two species of *Staphylococcus aureus* (N315 and Mu50) have been sequenced and are publicly available, for example at PATRIC (PATRIC: The VBI PathoSystems Resource Integration Center, Snyder et al., 2007). As would be understood by the skilled person, *Staphylococcus* proteins for use as antigens may also be identified in other public databases such as GenBank®, Swiss-Prot®, and TrEMBL®.

Antigens derived from *Streptococcus pneumoniae* that are contemplated for use in certain embodiments described herein include pneumolysin, PspA, choline-binding protein A (CbpA), NanA, NanB, SpnHL, PavA, LytA, Pht, and pilin proteins (RrgA; RrgB; RrgC). Antigenic proteins of *Streptococcus pneumoniae* are also known in the art and may be used as an antigen in some embodiments (see, e.g., Zysk et al., 2000). The complete genome sequence of a virulent strain of *Streptococcus pneumoniae* has been sequenced and, as would be understood by the skilled person, *S. pneumoniae* proteins for use herein may also be identified in other public databases such as GENBANK®, SWISS-PROT®, and TREMBL®. Proteins of particular interest for antigens according to the present disclosure include virulence factors and proteins predicted to be exposed at the surface of the pneumococci (see, e.g., Frolet et al., 2010).

Examples of bacterial antigens that may be used as antigens include, but are not limited to, *Actinomyces* polypeptides, *Bacillus* polypeptides, *Bacteroides* polypeptides, *Bordetella* polypeptides, *Bartonella* polypeptides, *Borrelia* polypeptides (e.g., *B. burgdorferi* OspA), *Brucella* polypeptides, *Campylobacter* polypeptides, Capnocytophaga polypeptides, *Chlamydia* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides (e.g., *H. influenzae* type b outer membrane protein), *Helicobacter* polypeptides, *Klebsiella* polypeptides, L-form bacteria polypeptides, *Leptospira* polypeptides, *Listeria* polypeptides, Mycobacteria polypeptides, *Mycoplasma* polypeptides, *Neisseria* polypeptides, *Neorickettsia* polypeptides, *Nocardia* polypeptides, *Pasteurella* polypeptides, Peptococcus polypeptides, *Peptostreptococcus* polypeptides, Pneumococcus polypeptides (i.e., *S. pneumoniae* polypeptides) (see description herein), *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, group A *streptococcus* polypeptides (e.g., *S. pyogenes* M proteins), group B *streptococcus* (*S. agalactiae*) polypeptides, *Treponema* polypeptides, and *Yersinia* polypeptides (e.g., *Y. pestis* F1 and V antigens).

Examples of fungal antigens include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite antigens include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, Giardia polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides. Examples of helminth parasite antigens include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides. (e.g., *P. falciparum* circumsporozoite (PfCSP)), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of ectoparasite antigens include, but are not limited to, polypeptides (including antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

2. Methods of Delivery

One of skill in the art would be well-equipped to construct a vector through standard recombinant techniques (see, for example, Sambrook et al., 2001 and Ausubel et al., 1996, both incorporated herein by reference) for the expression of the antigen receptors of the present disclosure. Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors, parvovirus vectors, polio virus vectors, vesicular stomatitis virus vectors, maraba virus vectors and group B adenovirus enadenotucirev vectors.

a. Viral Vectors

Viral vectors encoding an antigen receptor may be provided in certain aspects of the present disclosure. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor mediated-endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Retroviral vectors, which include gamma-retroviral vectors and lentiviral vectors, can permanently integrate into the host genome and enable long-term stable gene expression. Gamma-retroviral vectors are derived from the Moloney Murine Leukemia Virus (MMLV) or Murine Stem Cell Virus (MSCV) genomes while lentiviral vectors are derived from the human immunodeficiency virus (HIV) genome.

Gamma-retroviruses and lentiviruses are complex retroviruses, which, in addition to the common retroviral genes gag, pol, and env, contain other genes with regulatory or structural function. Both gamma-retroviral and lentiviral vectors are well known in the art (see, for example, U.S. Pat. Nos. 6,013,516, 5,994,136 and 9,669,049, and U.S. Patent Application 2019/0032011).

Recombinant gamma-retroviral vectors are capable of infecting dividing cells, while recombinant lentiviral vectors are capable of infecting both dividing and non-dividing cells. Gamma-retroviral and lentiviral vectors can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

b. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. A promoter used in the context of the present disclosure includes constitutive, inducible, and tissue-specific promoters.

(i) Promoter/Enhancers

The expression constructs provided herein comprise a promoter to drive expression of the antigen receptor. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30110 bp-upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the βlactamase (penicillinase), lactose and tryptophan (trp-) promoter systems. In addition to producing nucleic acid sequences of promoters and enhancers synthetically, sequences may be produced using recombinant cloning and/or nucleic acid amplification technology, including PCR™, in connection with the compositions disclosed herein. Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter, GADPH promoter, metallothionein promoter; and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). In certain embodiments, the promoter is CMV IE, dectin-1, dectin-2, human CD11c, F4/80, SM22, RSV, SV40, Ad MLP, beta-actin, MHC class I or MHC class II promoter, however any other promoter that is useful to drive expression of the therapeutic gene is applicable to the practice of the present disclosure.

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

(ii) Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Additionally, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the F2A (Foot-and-mouth disease virus 2A) or a "2A-like" sequence (e.g., Thosea asigna virus 2A; T2A).

(iii) Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively, a replication origin of other extrachromosomally replicating virus as described above or an autonomously replicating sequence (ARS) can be employed.

c. Selection and Screenable Markers

In some embodiments, cells containing a construct of the present disclosure may be identified in vitro or in vivo by including a marker in the expression vector. Such markers would confer an identifiable change to the cell permitting easy identification of cells containing the expression vector.

Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

E. Express REP

The genetically engineered T cells may then be expanded using an express REP method. The express REP method may comprise culture with feeder cells, such as pooled allogeneic irradiated PBMC feeder cells. The T cells and feeder cells may be at a ratio of 1:10, 1:25, 1:50, 1:100, 1:200, 1:500, particularly 1:200. The culture may comprise IL-2, such as 1-10,000 IU/mL IL-2, particularly 6000 IU/mL IL-2. In particular aspects, the REP step does not comprise anti-CD3 stimulation.

Rapid expansion provides an increase in the number of T-cells of at least about 50-fold (e.g., 50-, 60-, 70-, 80-, 90-, or 100-fold, or greater) over a period of about 10 to about 14 days, preferably about 14 days. More preferably, rapid expansion provides an increase of at least about 200-fold (e.g., 200-, 300-, 400-, 500-, 600-, 700-, 800-, 900-, or greater) over a period of about 10 to about 14 days, preferably about 14 days.

The expanded T cells may then be sorted using flow cytometry for the markers CD3, CD4, and CD8 as well as the gene of interest that the T cells are transduced with.

II. Treatment of Diseases

The present methods can facilitate the generation of a large number of highly functional T cells for cell immunotherapy. Thus, methods are provided herein for the treatment of diseases by the adoptive infusion of T cells.

In some embodiments, the present disclosure provides methods for immunotherapy comprising administering an effective amount of the T cells of the present disclosure. In one embodiment, a medical disease or disorder is treated by transfer of a T cell population that elicits an immune response. In certain embodiments of the present disclosure, cancer or infection is treated by transfer of a T cell population that elicits an immune response. Provided herein are methods for treating or delaying progression of cancer in an individual comprising administering to the individual an effective amount a T cell therapy. The present methods may be applied for the treatment of immune disorders, solid cancers, hematologic cancers, and viral infections.

Tumors for which the present treatment methods are useful include any malignant cell type, such as those found in a solid tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; and immunoproliferative small intestinal disease.

In certain embodiments of the present disclosure, T cells are delivered to an individual in need thereof, such as an individual that has cancer or an infection. The cells then enhance the individual's immune system to attack the respective cancer or pathogenic cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

In some embodiments, the subject can be administered nonmyeloablative lymphodepleting chemotherapy prior to the T cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m$^2$ fludarabine is administered for five days.

In certain embodiments, a growth factor that promotes the growth and activation of the T cells is administered to the subject either concomitantly with the T cells or subsequently to the T cells. The immune cell growth factor can be any suitable growth factor that promotes the growth and activation of the T cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of T cells can be administered by a number of routes, including parenteral administration, for example, intravenous, intraperitoneal, intramuscular, intrasternal, or intraarticular injection, or infusion. The therapeutically effective amount of T cells for use in adoptive cell therapy is that amount that achieves a desired effect in a subject being treated. For instance, this can be the amount of T cells necessary to inhibit advancement, or to cause regression of cancer, or which is capable of relieving symptoms caused by cancer.

The T cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of T cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8 \times 10^8$, at least $3.8 \times 10^9$, or at least $3.8 \times 10^{10}$ T cells/m$^2$ or a maximum dose of $1.5 \times 10^{11}$. In a certain embodiment, the dose used in the treatment of human subjects ranges from about $3.8 \times 10^9$ to about $3.8 \times 10^{10}$ T cells/m$^2$. The exact amount of T cells is readily determined by one of skill in the art based on the age, sex, and physiological condition of the subject. Effective doses can be extrapolated from dose-response curves derived from in vitro or animal model test systems.

The T cells may be administered in combination with one or more other therapeutic agents for the treatment of the immune-mediated disorder. Combination therapies can include, but are not limited to, one or more anti-microbial agents (for example, antibiotics, anti-viral agents and anti-fungal agents), anti-tumor agents (for example, fluorouracil, methotrexate, paclitaxel, fludarabine, etoposide, doxorubicin, or vincristine), immune-depleting agents (for example, fludarabine, etoposide, doxorubicin, or vincristine), immunosuppressive agents (for example, azathioprine, or glucocorticoids, such as dexamethasone or prednisone), anti-inflammatory agents (for example, glucocorticoids such as hydrocortisone, dexamethasone or prednisone, or non-steroidal anti-inflammatory agents such as acetylsalicylic acid, ibuprofen or naproxen sodium), cytokines (for example, interleukin-10 or transforming growth factor-beta), hormones (for example, estrogen), or a vaccine. In addition, immunosuppressive or tolerogenic agents including but not limited to calcineurin inhibitors (e.g., cyclosporin and tacrolimus); mTOR inhibitors (e.g., Rapamycin); mycophenolate mofetil, antibodies (e.g., recognizing CD3, CD4, CD40, CD154, CD45, IVIG, or B cells); chemotherapeutic agents (e.g., Methotrexate, Treosulfan, Busulfan); irradiation; or chemokines, interleukins or their inhibitors (e.g., BAFF, IL-2, anti-IL-2R, IL-4, JAK kinase inhibitors) can be administered. Such additional pharmaceutical agents can be administered before, during, or after administration of the T cells, depending on the desired effect. This administration of the cells and the agent can be by the same route or by different routes, and either at the same site or at a different site.

A. Pharmaceutical Preparations

Where clinical application of a therapeutic composition containing an inhibitory antibody is undertaken, it will generally be beneficial to prepare a pharmaceutical or therapeutic composition appropriate for the intended application.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The therapeutic compositions of the present embodiments are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

B. Combination Treatments

In certain embodiments, the compositions and methods of the present embodiments involve a T cell therapy, in combination with a second or additional therapy. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an antibody or antibody fragment and a second therapy. A tissue, tumor, or cell can be contacted with one or more compositions or pharmacological formulation(s) comprising one or more of the agents (i.e., antibody or antibody fragment or an anti-cancer agent), or by contacting the tissue, tumor, and/or cell with two or more distinct compositions or formulations, wherein one composition provides 1) an antibody or antibody fragment, 2) an anti-cancer agent, or 3) both an antibody or antibody fragment and an anti-cancer agent. Also, it is contemplated that such a combination therapy can be used in conjunction with chemotherapy, radiotherapy, surgical therapy, or immuno-therapy.

The terms "contacted" and "exposed," when applied to a cell, are used herein to describe the process by which a therapeutic construct and a chemotherapeutic or radiothera-peutic agent are delivered to a target cell or are placed in direct juxtaposition with the target cell. To achieve cell killing, for example, both agents are delivered to a cell in a combined amount effective to kill the cell or prevent it from dividing.

An inhibitory antibody may be administered before, dur-ing, after, or in various combinations relative to an anti-cancer treatment. The administrations may be in intervals ranging from concurrently to minutes to days to weeks. In embodiments where the antibody or antibody fragment is provided to a patient separately from an anti-cancer agent, one would generally ensure that a significant period of time did not expire between the time of each delivery, such that the two compounds would still be able to exert an advan-tageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment signifi-cantly where several days (2, 3, 4, 5, 6, or 7) to several weeks (1, 2, 3, 4, 5, 6, 7, or 8) lapse between respective adminis-trations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a T cell therapy is "A" and an anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/B | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards, such as chlorambucil, chlo-rnaphazine, cholophosphamide, estramustine, ifosfamide, mechlorethamine, mechlorethamine oxide hydrochloride, melphalan, novembichin, phenesterine, prednimustine, tro-fosfamide, and uracil mustard; nitrosureas, such as carmus-tine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chro-moprotein enediyne antiobiotic chromophores, aclacino-mysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including mor-pholino-doxorubicin, cyanomorpholino-doxorubicin, 2-pyr-rolino-doxorubicin and deoxydoxorubicin), epirubicin, eso-rubicin, idarubicin, marcellomycin, mitomycins, such as mitomycin C, mycophenolic acid, nogalarnycin, olivomy-cins, peplomycin, potfiromycin, puromycin, quelamycin, rodorubicin, streptonigrin, streptozocin, tubercidin, uben-imex, zinostatin, and zorubicin; anti-metabolites, such as methotrexate and 5-fluorouracil (5-FU); folic acid ana-logues, such as denopterin, pteropterin, and trimetrexate; purine analogs, such as fludarabine, 6-mercaptopurine, thia-miprine, and thioguanine; pyrimidine analogs, such as ancit-abine, azacitidine, 6-azauridine, carmofur, cytarabine, dide-oxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diazi-quone; elformithine; elliptinium acetate; an epothilone; eto-glucid; gallium nitrate; hydroxyurea; lentinan; lonidainine; maytansinoids, such as maytansine and ansamitocins; mitoguazone; mitoxantrone; mopidanmol; nitraerine; pen-tostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; manno-mustine; mitobronitol; mitolactol; pipobroman; gacytosine; arabinoside ("Ara-C"); cyclophosphamide; taxoids, e.g., paclitaxel and docetaxel gemcitabine; 6-thioguanine; mer-captopurine; platinum coordination complexes, such as cis-platin, oxaliplatin, and carboplatin; vinblastine; platinum; etoposide (VP-16); ifosfamide; mitoxantrone; vincristine; vinorelbine; novantrone; teniposide; edatrexate; daunomy-cin; aminopterin; xeloda; ibandronate; irinotecan (e.g., CPT-11); topoisomerase inhibitor RFS 2000; difluorometlhylor-nithine (DMFO); retinoids, such as retinoic acid; capecitabine; carboplatin, procarbazine, plicomycin, gemcitabien, navelbine, farnesyl-protein tansferase inhibi-tors, transplatinum, and pharmaceutically acceptable salts, acids, or derivatives of any of the above, 2. Radiotherapy Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradia-tion. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immu-notherapies may be used in combination or in conjunction with methods of the embodiments. In the context of cancer treatment, immunotherapeutics, generally, rely on the use of immune effector cells and molecules to target and destroy cancer cells. The immune effector may be, for example, comprise an antibody or chimeric antigen receptor (CAR) specific for some marker on the surface of a tumor cell. In further aspects, the therapy may comprise administration of T-cell or NK-cells that are targeted to specific cancer cell. Such cells can be engineered or merely selected for anti-cancer cell activity.

In some aspects, an antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a break-through approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher 2014; Leal et al., 2014). Tar-geted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA®

(trastuzumab emtansine or T-DM1) in 2013 by FDA vali-dated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating mol-ecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investiga-tion or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and mono-clonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints are mol-ecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lympho-cyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Par-doll, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example, it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95(17): 10067-10071; Camacho et al. (2004) J Clin Oncology 22(145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017, 114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

III. Kits and Diagnostics

In various aspects of the embodiments, a kit is envisioned containing therapeutic agents and/or other therapeutic and delivery agents. In some embodiments, the present embodiments contemplates a kit for preparing and/or administering a therapy of the embodiments. The kit may comprise one or more sealed vials containing any of the pharmaceutical compositions of the present embodiments. The kit may include, for example, a population of T cells as well as reagents to prepare, formulate, and/or administer the components of the embodiments or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a therapeutic agent.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Production and Characterization of Anti-41BB Antibodies

As shown in FIG. 1, five tumor fragments (between 1 to 3 mm2) were set up for TIL culture for each condition in each presented cancer, in media containing 30 ng/mL of anti-CD3 (OKT3), and 10 ug/mL of anti-4-1BB (Positive control, or two anti-4-IBB clones 37599.1.a or 37605.1.a, or a control without anti-4-1BB) and 6000 IU/mL of IL-2 in TIL complete media in a G-Rex 10 device.

Figure 2A:
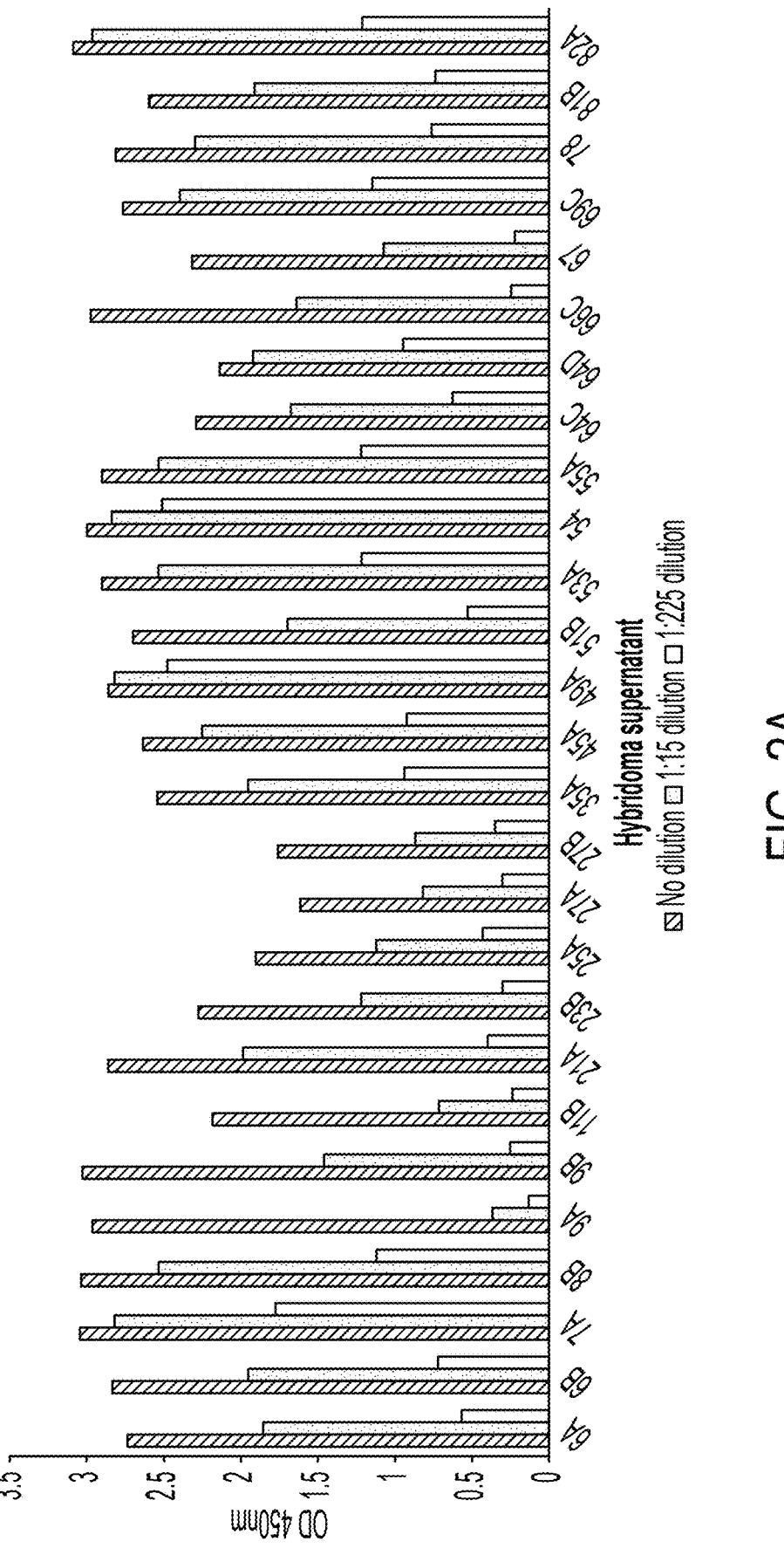
FIGS. 2A-2C.
Figure 2B:
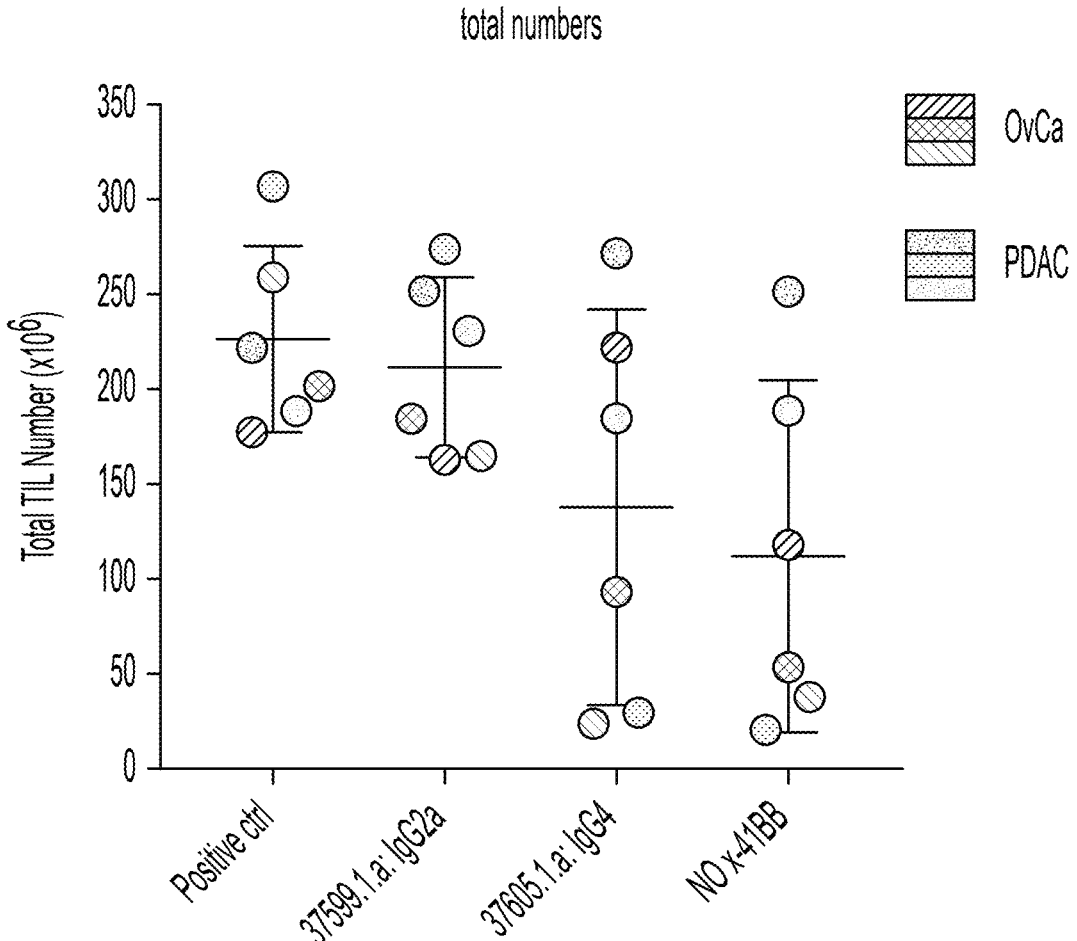
Figure 2C:
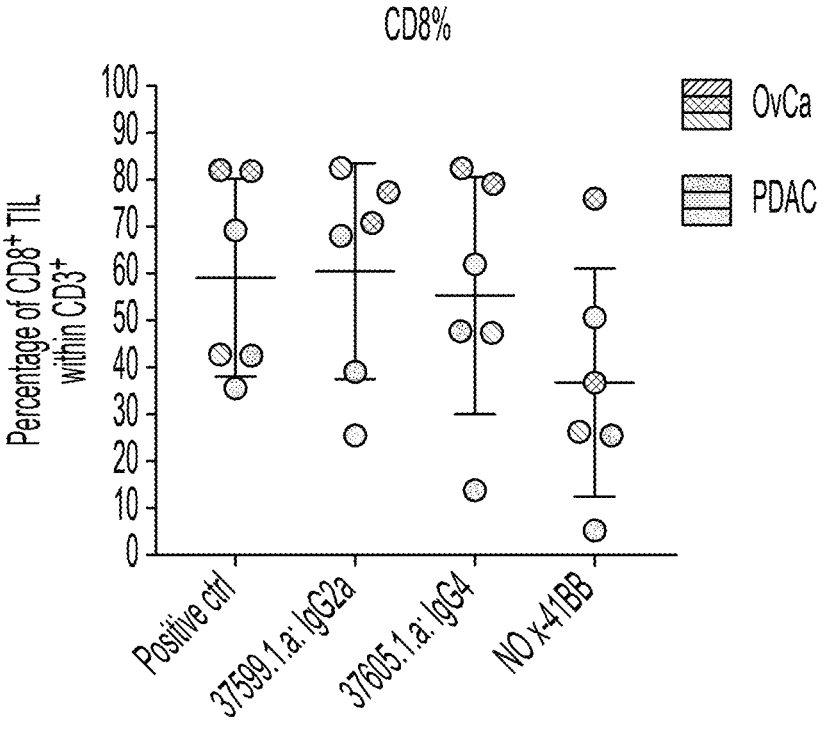
Figure 2C:
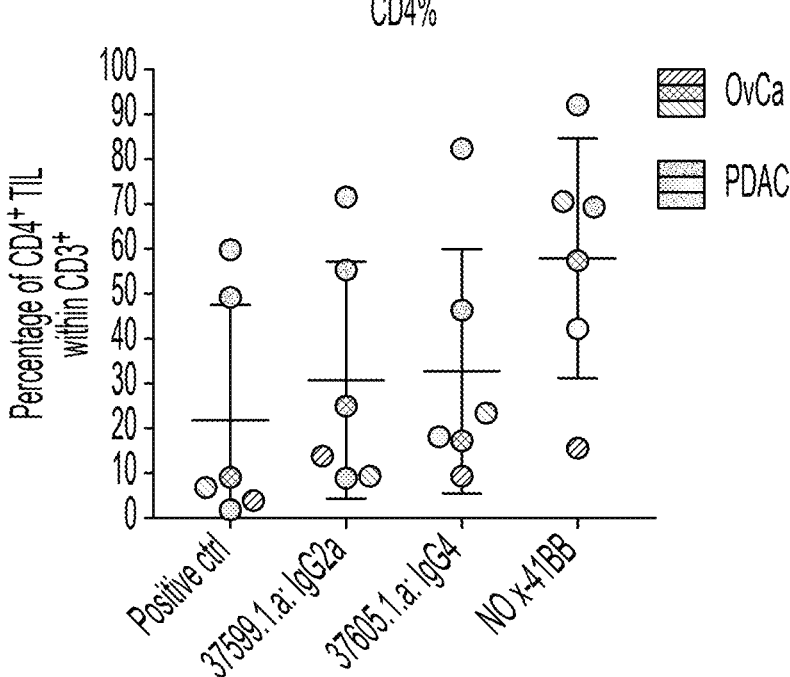

Half media changes were performed every 3 to 4 days (20 mL of TIL complete media and 6000 IU/mL of IL-2) until culture was stopped for reaching confluency or terminated for no growth at 3 weeks. At the termination of the culture cells were counted and phenotyped. As shown in FIG. 2A, clone 375991.a gave similar TIL yields as the positive control, and comparable percentages of CD8 and CD4 T cells across the 3 ovarian cancer and 4 pancreatic cancer tumor samples used for this study.

Next, the express REP protocol started at Day −5 with thawing, counting and plating at $1.5 \times 10^6$/ml. At day −3, the cells were harvested, counted, and replaced on anti-CD3 coated tissue culture plates. At day −1, cells were harvested and viral transduction was performed, utilizing retroviral vector bound to retronectin plates, and facilitated by spinning the T cells onto the viral supernatant coated plates. Cells were incubated overnight at 37° C.

At day 0, the REP was setup using G-Rex 100M flasks using $1 \times 10^9$ irradiated feeders, $2.5$-$5 \times 10^6$ TILs, and 400 mL of media with IL-2. At day 4 or 5, 200 mL of fresh media containing 3000 IU/mL IL-2 was added. At day 7, cells were counted and subcultured into new flasks if needed. Media containing 3000 IU/mL IL-2 was added to each flask to achieve a total volume of 1000 mL per flask. At day 9 or 10, IL-2 was added to the flasks for a final concentration of 3000 IU/mL. Similarly, at day 11 or 12, IL-2 was added to the flasks for a final concentration of 3000 IU/mL. Samples were then removed for sterility assessment. At day 14, the cells were transferred in bags using the Baxapump and harvested on the COBE 2991. Thus, the present methods of combined three-way signal pre-activation, transduction, and express REP resulted in a large number of genetically modified TILs for cell therapy.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ausubel et al., *Current Protocols in Molecular Biology,*
   *Greene Publishing Associates and John*
Wiley & Sons, N Y, 1994
Chothia et al., EMBO J. 7:3745, 1988.
Cohen et al. *J Immunol.* 175:5799-5808, 2005.
Fedorov et al., *Sci. Transl. Medicine,* 5(215) 2013.
Harao et al., Cancer Immunology Research, 439-445, 2017.
Heemskerk et al. *Hum Gene Ther.* 19:496-510, 2008.
International Patent Publication No. WO2014/055668
International Patent Publication No. WO99/40188
Janeway et al, *Immunobiology: The Immune System in*
   *Health and Disease,* 3$^{rd}$ Ed., Current
Johnson et al. *Blood* 114:535-46, 2009.
Jores et al., *PNAS U.S.A.* 87:9138, 1990.
Lefranc et al., Dev. Comp. Immunol. 27:55, 2003.
Li, *Nat Biotechnol.* 23:349-354, 2005.
Linnemann et al., 2015
Liu et al., *Mol. Cancer Ther.,* 2:1341-1350, 2003.
Mellman et al., *Nature* 480:480-489, 2011.

Pardoll, Nature Rev *Cancer,* 12:252-264, 2012.
Parkhurst et al. *Clin Cancer Res.* 15: 169-180, 2009.
Sakellariou et al., Cancer Immunology, 2019.
Sakellariou et al., Clin Cancer Res, 23(23): 7263-7275, 2017.
Sambrook et al., *Molecular Cloning: A Laboratory Manual,*
   3$^{rd}$ ed., Cold Spring Harbor Press,
Cold Spring Harbor, N.Y. 2001
U.S. Pat. No. 5,091,513
U.S. Pat. No. 5,091,513
U.S. Pat. No. 5,994,136
U.S. Pat. No. 5,994,136
U.S. Pat. No. 6,013,516
U.S. Pat. No. 6,410,319
U.S. Pat. No. 6,881,557
U.S. Pat. No. 6,946,546
U.S. Pat. No. 7,109,304
U.S. Patent Publication No. 20050214860
Varela-Rohena et al. *Nat Med.* 14: 1390-1395, 2008.
Vinay and Kwon, Mol Cancer Ther, 11(5): 1062-70, 2012.

What is claimed is:

1. An ex vivo method for activation and expansion of T cells comprising:

(a) pre-activating a starting population of T cells in the presence of an agonistic 4-1BB antibody and an anti-CD3 antibody to generate pre-activated T cells;

(b) further activating the pre-activated T cells in the presence of IL-2 and anti-CD3 antibody, wherein the activation is performed in the absence of the agonistic 4-1BB of step (a) antibody, to generate activated T cells;

(c) genetically modifying the activated T cells to obtain genetically modified T cells; and (d) expanding the genetically modified T cells in the presence of IL-2 and feeder cells to produce a population of expanded T cells, wherein steps (a)-(d) are performed in less than 6 weeks, wherein the agonistic 4-1BB antibody is an isolated monoclonal antibody, wherein the antibody specifically binds to 4-1BB and comprises:

(a) a first $V_H$ CDR is identical to SEQ ID NO: 3;

(b) a second $V_H$ CDR is identical to SEQ ID NO: 5;

(c) a third $V_H$ CDR is identical to SEQ ID NO: 7;

(d) a first $V_L$ CDR is identical to SEQ ID NO: 11;

(e) a second $V_L$ CDR is identical to SEQ ID NO: 13; and (f) a third $V_L$ CDR is identical to SEQ ID NO: 15; or (a) a first $V_H$ CDR is identical to SEQ ID NO: 19;

(b) a second $V_H$ CDR is identical to SEQ ID NO: 21;

(c) a third $V_H$ CDR is identical to SEQ ID NO: 23;

(d) a first $V_L$ CDR is identical to SEQ ID NO: 27;

(e) a second $V_L$ CDR is identical to SEQ ID NO: 29; and (f) a third $V_L$ CDR is identical to SEQ ID NO: 31; or (a) a first $V_H$ CDR is identical to SEQ ID NO: 35;

(b) a second $V_H$ CDR is identical to SEQ ID NO: 37;

(c) a third $V_H$ CDR is identical to SEQ ID NO: 39;

(d) a first $V_L$ CDR is identical to SEQ ID NO: 43;

(e) a second $V_L$ CDR is identical to SEQ ID NO: 45; and (f) a third $V_L$ CDR is identical to SEQ ID NO: 47; or
(a) a first $V_H$ CDR is identical to SEQ ID NO: 51;
(b) a second $V_H$ CDR is identical to SEQ ID NO: 53;
(c) a third $V_H$ CDR is identical to SEQ ID NO: 55;
(d) a first $V_L$ CDR is identical to SEQ ID NO: 59;
(e) a second $V_L$ CDR is identical to SEQ ID NO: 61; and
(f) a third $V_L$ CDR is identical to SEQ ID NO: 63.

2. The method of claim 1, wherein the starting population of T cells comprises tumor infiltrating lymphocytes (TILs) derived from tumor tissue.

3. The method of claim 1, wherein pre-activating is further in the presence of IL-2.

4. The method of claim 3, wherein the IL-2 is human recombinant IL-2 at a concentration of 6,000 IU/mL.

5. The method of claim 1, wherein pre-activating is performed for 10-16 days.

6. The method of claim 1, wherein pre-activating is performed in a gas permeable bioreactor.

7. The method of claim 1, wherein the agonistic 4-1BB antibody comprises a $V_H$ domain at least about 90% identical to the $V_H$ domain of clone 54 (SEQ ID NO: 2) and a $V_L$ domain at least about 90% identical to the $V_L$ domain of clone 54 (SEQ ID NO: 10).

8. The method of claim 1, wherein the agonistic 4-1BB antibody comprises a $V_H$ domain at least about 90% identical to the $V_H$ domain of clone 135B (SEQ ID NO: 18) and a $V_L$ domain at least about 90% identical to the $V_L$ domain of clone 135B (SEQ ID NO: 26).

9. The method of claim 1, wherein the agonistic 4-1BB antibody comprises a $V_H$ domain at least about 90% identical to the $V_H$ domain of clone 138 (SEQ ID NO: 34) and a $V_L$ domain at least about 90% identical to the $V_L$ domain of clone 138 (SEQ ID NO: 42).

10. The method of claim 1, wherein the agonistic 4-1BB antibody comprises a $V_H$ domain at least about 90% identical to the $V_H$ domain of clone 49A (SEQ ID NO: 50) and a $V_L$ domain at least about 90% identical to the $V_L$ domain of clone 49A (SEQ ID NO: 58).

11. The method of claim 1, wherein the method further comprises a resting step comprising culturing the pre-activated T cells in the presence of IL-2 prior to step (b).

12. The method of claim 11, wherein the IL-2 is at a concentration of 6000 IU/mL.

13. The method of claim 1, wherein the anti-CD3 antibody is bound to a surface culture plate.

14. The method of claim 1, wherein genetically modifying comprises transducing the activated T cells with a viral construct.

15. The method of claim 14, wherein the viral construct encodes a encodes a chemokine, cytokine, or costimulatory domain.

16. The method of claim 15, wherein the chemokine binds to CXCR2.

17. The method of claim 1, wherein the IL-2 in step (d) is at a concentration of 3000 IU/mL.

18. A pharmaceutical composition comprising a population of expanded T cells produced by claim 1 and a pharmaceutically acceptable carrier.

\* \* \* \* \*

SEQUENCE LISTING

<160> NUMBER OF SEQ ID NOS: 64

<210> SEQ ID NO 1
<211> LENGTH: 429
<212> TYPE: DNA
<213> ORGANISM: Artificial sequence
<220> FEATURE:
<223> OTHER INFORMATION: Synthetic antibody

<400> SEQUENCE: 1

```
gagttccagc tgcagcagtc tggacctgag ctggtgaagc ctggcgcttc agtgaagata      60
tcctgcaagg cttctggtta ctcattcact gactacaaca tgaactgggt gaagcagagc     120
aatggaaaga gccttgagtg gattggagta attaatccta actatggtac tactagctac     180
aatcagaagt tcaagggcaa ggccacattt actgtagacc aatcttccag cacagcctac     240
atgcagctca acagcctgac atctgaggac tctgcagtct attactgtgc aagatccccg     300
gtagaggact actttgacta ctggggccaa ggcaccactc tcacagtctc ctcagccaaa     360
acaacagccc catcggtcta tccactggcc cctgtgtgtg gaggtacaac tggctcctcg     420
gtgactcta                                                             429
```

<210> SEQ ID NO 2
<211> LENGTH: 143
<212> TYPE: PRT
<213> ORGANISM: Artificial sequence
<220> FEATURE:
<223> OTHER INFORMATION: Synthetic antibody

<400> SEQUENCE: 2

```
Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser Asn Gly Lys Ser Leu Glu Trp Ile
        35                  40                  45

Gly Val Ile Asn Pro Asn Tyr Gly Thr Thr Ser Tyr Asn Gln Lys Phe
    50                  55                  60

Lys Gly Lys Ala Thr Phe Thr Val Asp Gln Ser Ser Ser Thr Ala Tyr
65                  70                  75                  80
```

-continued

```
Met Gln Leu Asn Ser Leu Thr Ser Glu Asp Ser Ala Val Tyr Tyr Cys
                85                  90                  95

Ala Arg Ser Pro Val Glu Asp Tyr Phe Asp Tyr Trp Gly Gln Gly Thr
            100                 105                 110

Thr Leu Thr Val Ser Ser Ala Lys Thr Thr Ala Pro Ser Val Tyr Pro
        115                 120                 125

Leu Ala Pro Val Cys Gly Gly Thr Thr Gly Ser Ser Val Thr Leu
    130                 135                 140
```

```
<210> SEQ ID NO 3
<211> LENGTH: 8
<212> TYPE: PRT
<213> ORGANISM: Artificial sequence
<220> FEATURE:
<223> OTHER INFORMATION: Synthetic antibody

<400> SEQUENCE: 3

Gly Tyr Ser Phe Thr Asp Tyr Asn
1               5
```

```
<210> SEQ ID NO 4
<211> LENGTH: 24
<212> TYPE: DNA
<213> ORGANISM: Artificial sequence
<220> FEATURE:
<223> OTHER INFORMATION: Synthetic antibody

<400> SEQUENCE: 4
ggttactcat tcactgacta caac                                          24
```

```
<210> SEQ ID NO 5
<211> LENGTH: 8
<212> TYPE: PRT
<213> ORGANISM: Artificial sequence
<220> FEATURE:
<223> OTHER INFORMATION: Synthetic antibody

<400> SEQUENCE: 5

Ile Asn Pro Asn Tyr Gly Thr Thr
1               5
```

```
<210> SEQ ID NO 6
<211> LENGTH: 24
<212> TYPE: DNA
<213> ORGANISM: Artificial sequence
<220> FEATURE:
<223> OTHER INFORMATION: Synthetic antibody

<400> SEQUENCE: 6
attaatccta actatggtac tact                                          24
```

```
<210> SEQ ID NO 7
<211> LENGTH: 11
<212> TYPE: PRT
<213> ORGANISM: Artificial sequence
<220> FEATURE:
<223> OTHER INFORMATION: Synthetic antibody

<400> SEQUENCE: 7

Ala Arg Ser Pro Val Glu Asp Tyr Phe Asp Tyr
1               5                   10
```

```
<210> SEQ ID NO 8
<211> LENGTH: 33
<212> TYPE: DNA
```

-continued

```
<213> ORGANISM: Artificial sequence
<220> FEATURE:
<223> OTHER INFORMATION: Synthetic antibody

<400> SEQUENCE: 8
gcaagatccc cggtagagga ctactttgac tac                              33

<210> SEQ ID NO 9
<211> LENGTH: 380
<212> TYPE: DNA
<213> ORGANISM: Artificial sequence
<220> FEATURE:
<223> OTHER INFORMATION: Synthetic antibody

<400> SEQUENCE: 9
gaaaatgtgc tcacccagtc tccagcaatc atgtctgcat ctccagggga aaaggtcacc    60
atgacctgca gggccaggtc aagtgtaagt tccagttact tgcactggta ccagcagaag   120
tcaggtgcct cccccaaact ctggatttat agcacatcca acttggcttc tggagtccct   180
gctcgcttca gtggcagtgg gtctgggacc tcttactctc tcacaatcag cagtgtggag   240
gctgaagatg ctgccactta ttactgccag cagtacagtg gttacccact catcacgttc   300
ggtgctggga ccaagctgga gctgaaacgg gctgatgctg caccaactgt atccatcttc   360
ccaccatcca gtgagcagtt                                              380

<210> SEQ ID NO 10
<211> LENGTH: 126
<212> TYPE: PRT
<213> ORGANISM: Artificial sequence
<220> FEATURE:
<223> OTHER INFORMATION: Synthetic antibody

<400> SEQUENCE: 10

Glu Asn Val Leu Thr Gln Ser Pro Ala Ile Met Ser Ala Ser Pro Gly
1               5                   10                  15

Glu Lys Val Thr Met Thr Cys Arg Ala Arg Ser Ser Val Ser Ser Ser
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Ile Thr Phe Gly Ala Gly Thr Lys Leu Glu Leu Lys Arg Ala Asp
            100                 105                 110

Ala Ala Pro Thr Val Ser Ile Phe Pro Pro Ser Ser Glu Gln
        115                 120                 125

<210> SEQ ID NO 11
<211> LENGTH: 7
<212> TYPE: PRT
<213> ORGANISM: Artificial sequence
<220> FEATURE:
<223> OTHER INFORMATION: Synthetic antibody

<400> SEQUENCE: 11

Ser Ser Val Ser Ser Ser Tyr
1               5
```

<210> SEQ ID NO 12
<211> LENGTH: 21
<212> TYPE: DNA
<213> ORGANISM: Artificial sequence
<220> FEATURE:
<223> OTHER INFORMATION: Synthetic antibody

<400> SEQUENCE: 12
tcaagtgtaa gttccagtta c                                                    21

<210> SEQ ID NO 13
<211> LENGTH: 3
<212> TYPE: PRT
<213> ORGANISM: Artificial sequence
<220> FEATURE:
<223> OTHER INFORMATION: Synthetic antibody

<400> SEQUENCE: 13

Ser Thr Ser
1

<210> SEQ ID NO 14
<211> LENGTH: 9
<212> TYPE: DNA
<213> ORGANISM: Artificial sequence
<220> FEATURE:
<223> OTHER INFORMATION: Synthetic antibody

<400> SEQUENCE: 14 agcacatcc                                                                   9

<210> SEQ ID NO 15
<211> LENGTH: 10
<212> TYPE: PRT
<213> ORGANISM: Artificial sequence
<220> FEATURE:
<223> OTHER INFORMATION: Synthetic antibody

<400> SEQUENCE: 15

Gln Gln Tyr Ser Gly Tyr Pro Leu Ile Thr
1               5                   10

<210> SEQ ID NO 16
<211> LENGTH: 30
<212> TYPE: DNA
<213> ORGANISM: Artificial sequence
<220> FEATURE:
<223> OTHER INFORMATION: Synthetic antibody

<400> SEQUENCE: 16
cagcagtaca gtggttaccc actcatcacg                                           30

<210> SEQ ID NO 17
<211> LENGTH: 363
<212> TYPE: DNA
<213> ORGANISM: Artificial sequence
<220> FEATURE:
<223> OTHER INFORMATION: Synthetic antibody

<400> SEQUENCE: 17
aggtgaagct gcagcagtca ggacctgagc tggtgaagcc tggggcttca gtgaagatat        60
cctgtaaggc ttctggatac acgttcactg actactacat gaactgggtg aagcagagcc       120
atggaaagag ccttgagtgg attggagata ttaatcctaa caatgatggt actacctact       180
acaaccagaa gttcaagggc aaggccacat tgactgtaga caagtcctcc agcacagcct       240

-continued

```
acatggagct ccgcagcctg acatctgagg actctgcagt ctattactgt gcaagatccc     300
tctacggtag tagctactac tttgactact ggggccaagg caccactctc acagtctcct     360
cag                                                                    363
```

```
<210> SEQ ID NO 18
<211> LENGTH: 120
<212> TYPE: PRT
<213> ORGANISM: Artificial sequence
<220> FEATURE:
<223> OTHER INFORMATION: Synthetic antibody

<400> SEQUENCE: 18

Val Lys Leu Gln Gln Ser Gly Pro Glu Leu Val Lys Pro Gly Ala Ser
1               5                   10                  15

Val Lys Ile Ser Cys Lys Ala Ser Gly Tyr Thr Phe Thr Asp Tyr Tyr
            20                  25                  30

Met Asn Trp Val Lys Gln Ser His Gly Lys Ser Leu Glu Trp Ile Gly
        35                  40                  45

Asp Ile Asn Pro Asn Asn Asp Gly Thr Thr Tyr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Leu Tyr Gly Ser Ser Tyr Tyr Phe Asp Tyr Trp Gly Gln
            100                 105                 110

Gly Thr Thr Leu Thr Val Ser Ser
        115                 120
```

```
<210> SEQ ID NO 19
<211> LENGTH: 8
<212> TYPE: PRT
<213> ORGANISM: Artificial sequence
<220> FEATURE:
<223> OTHER INFORMATION: Synthetic antibody

<400> SEQUENCE: 19

Gly Tyr Thr Phe Thr Asp Tyr Tyr
1               5
```

```
<210> SEQ ID NO 20
<211> LENGTH: 24
<212> TYPE: DNA
<213> ORGANISM: Artificial sequence
<220> FEATURE:
<223> OTHER INFORMATION: Synthetic antibody

<400> SEQUENCE: 20
ggatacacgt tcactgacta ctac                                             24
```

```
<210> SEQ ID NO 21
<211> LENGTH: 8
<212> TYPE: PRT
<213> ORGANISM: Artificial sequence
<220> FEATURE:
<223> OTHER INFORMATION: Synthetic antibody

<400> SEQUENCE: 21

Ile Asn Pro Asn Asn Asp Gly Thr
1               5
```

-continued

```
<210> SEQ ID NO 22
<211> LENGTH: 24
<212> TYPE: DNA
<213> ORGANISM: Artificial sequence
<220> FEATURE:
<223> OTHER INFORMATION: Synthetic antibody

<400> SEQUENCE: 22
attaatccta acaatgatgg tact                                          24

<210> SEQ ID NO 23
<211> LENGTH: 13
<212> TYPE: PRT
<213> ORGANISM: Artificial sequence
<220> FEATURE:
<223> OTHER INFORMATION: Synthetic antibody

<400> SEQUENCE: 23

Ala Arg Ser Leu Tyr Gly Ser Ser Tyr Tyr Phe Asp Tyr
1               5                   10

<210> SEQ ID NO 24
<211> LENGTH: 39
<212> TYPE: DNA
<213> ORGANISM: Artificial sequence
<220> FEATURE:
<223> OTHER INFORMATION: Synthetic antibody

<400> SEQUENCE: 24
gcaagatccc tctacggtag tagctactac tttgactac                          39

<210> SEQ ID NO 25
<211> LENGTH: 334
<212> TYPE: DNA
<213> ORGANISM: Artificial sequence
<220> FEATURE:
<223> OTHER INFORMATION: Synthetic antibody

<400> SEQUENCE: 25
gatattgtga tgacacagtc tcctgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
gggatcccag ccaggtttag tggcagtggg tctgggacag acttcaccct caacatccat   240
cctgtggagg aggaggatgc tgcaacctat tactgtcagc aaagtaatga ggacccgtgg   300
acgttcggtg gaggcaccaa gctggaaatc aaac                              334

<210> SEQ ID NO 26
<211> LENGTH: 111
<212> TYPE: PRT
<213> ORGANISM: Artificial sequence
<220> FEATURE:
<223> OTHER INFORMATION: Synthetic antibody

<400> SEQUENCE: 26

Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45
```

```
Arg Leu Leu Ile Tyr Leu Val Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
                100                 105                 110
```

```
<210> SEQ ID NO 27
<211> LENGTH: 10
<212> TYPE: PRT
<213> ORGANISM: Artificial sequence
<220> FEATURE:
<223> OTHER INFORMATION: Synthetic antibody

<400> SEQUENCE: 27

Lys Ser Val Ser Thr Ser Gly Tyr Ser Tyr
1               5                   10
```

```
<210> SEQ ID NO 28
<211> LENGTH: 30
<212> TYPE: DNA
<213> ORGANISM: Artificial sequence
<220> FEATURE:
<223> OTHER INFORMATION: Synthetic antibody

<400> SEQUENCE: 28
aaaagtgtca gtacatctgg ctatagttat                               30
```

```
<210> SEQ ID NO 29
<211> LENGTH: 3
<212> TYPE: PRT
<213> ORGANISM: Artificial sequence
<220> FEATURE:
<223> OTHER INFORMATION: Synthetic antibody

<400> SEQUENCE: 29

Leu Val Ser
1
```

```
<210> SEQ ID NO 30
<211> LENGTH: 9
<212> TYPE: DNA
<213> ORGANISM: Artificial sequence
<220> FEATURE:
<223> OTHER INFORMATION: Synthetic antibody

<400> SEQUENCE: 30 cttgtatcc                                                       9
```

```
<210> SEQ ID NO 31
<211> LENGTH: 9
<212> TYPE: PRT
<213> ORGANISM: Artificial sequence
<220> FEATURE:
<223> OTHER INFORMATION: Synthetic antibody

<400> SEQUENCE: 31

Gln Gln Ser Asn Glu Asp Pro Trp Thr
1               5
```

```
<210> SEQ ID NO 32
<211> LENGTH: 27
```

-continued

```
<212> TYPE: DNA
<213> ORGANISM: Artificial sequence
<220> FEATURE:
<223> OTHER INFORMATION: Synthetic antibody

<400> SEQUENCE: 32
cagcaaagta atgaggaccc gtggacg                                          27

<210> SEQ ID NO 33
<211> LENGTH: 354
<212> TYPE: DNA
<213> ORGANISM: Artificial sequence
<220> FEATURE:
<223> OTHER INFORMATION: Synthetic antibody

<400> SEQUENCE: 33
aggtgcagct gcaggagtct gggggaggct tagtgaagcc tggagggtcc ctgaaactct      60
cctgtgcagc ctctggattc actttcagtg actatggaat gcactgggtt cgtcaggctc     120
cagagaaggg gctggagtgg gttgcataca ttagtagtgg cagtaattcc atctactatg     180
cagacacagt gacgggccga ttcaccatct ccagagacaa tgccaagaac accctgttcc     240
tgcaaatgac cagtctgagg tctgaggaca cggccatgta ttactgtgcc tcgaataatg     300
gttacttcta ctttgactac tggggccaag gcaccactct cacagtctcc tcag            354

<210> SEQ ID NO 34
<211> LENGTH: 117
<212> TYPE: PRT
<213> ORGANISM: Artificial sequence
<220> FEATURE:
<223> OTHER INFORMATION: Synthetic antibody

<400> SEQUENCE: 34

Val Gln Leu Gln Glu Ser Gly Gly Gly Leu Val Lys Pro Gly Gly Ser
1               5                   10                  15

Leu Lys Leu Ser Cys Ala Ala Ser Gly Phe Thr Phe Ser Asp Tyr Gly
            20                  25                  30

Met His Trp Val Arg Gln Ala Pro Glu Lys Gly Leu Glu Trp Val Ala
        35                  40                  45

Tyr Ile Ser Ser Gly Ser Asn Ser Ile Tyr Tyr Ala Asp Thr Val Thr
    50                  55                  60

Gly Arg Phe Thr Ile Ser Arg Asp Asn Ala Lys Asn Thr Leu Phe Leu
65                  70                  75                  80

Gln Met Thr Ser Leu Arg Ser Glu Asp Thr Ala Met Tyr Tyr Cys Ala
                85                  90                  95

Ser Asn Asn Gly Tyr Phe Tyr Phe Asp Tyr Trp Gly Gln Gly Thr Thr
            100                 105                 110

Leu Thr Val Ser Ser
        115

<210> SEQ ID NO 35
<211> LENGTH: 8
<212> TYPE: PRT
<213> ORGANISM: Artificial sequence
<220> FEATURE:
<223> OTHER INFORMATION: Synthetic antibody

<400> SEQUENCE: 35

Gly Phe Thr Phe Ser Thr Tyr Gly
1               5
```

-continued

<210> SEQ ID NO 36
<211> LENGTH: 24
<212> TYPE: DNA
<213> ORGANISM: Artificial sequence
<220> FEATURE:
<223> OTHER INFORMATION: Synthetic antibody

<400> SEQUENCE: 36
ggattcactt tcagtgacta tgga                                                24

<210> SEQ ID NO 37
<211> LENGTH: 8
<212> TYPE: PRT
<213> ORGANISM: Artificial sequence
<220> FEATURE:
<223> OTHER INFORMATION: Synthetic antibody

<400> SEQUENCE: 37

Ile Ser Ser Gly Ser Asn Ser Ile
1               5

<210> SEQ ID NO 38
<211> LENGTH: 24
<212> TYPE: DNA
<213> ORGANISM: Artificial sequence
<220> FEATURE:
<223> OTHER INFORMATION: Synthetic antibody

<400> SEQUENCE: 38
attagtagtg gcagtaattc catc                                                24

<210> SEQ ID NO 39
<211> LENGTH: 11
<212> TYPE: PRT
<213> ORGANISM: Artificial sequence
<220> FEATURE:
<223> OTHER INFORMATION: Synthetic antibody

<400> SEQUENCE: 39

Ala Ser Asn Asn Gly Tyr Phe Tyr Phe Asp Tyr
1               5                   10

<210> SEQ ID NO 40
<211> LENGTH: 33
<212> TYPE: DNA
<213> ORGANISM: Artificial sequence
<220> FEATURE:
<223> OTHER INFORMATION: Synthetic antibody

<400> SEQUENCE: 40
gcctcgaata atggttactt ctactttgac tac                                      33

<210> SEQ ID NO 41
<211> LENGTH: 316
<212> TYPE: DNA
<213> ORGANISM: Artificial sequence
<220> FEATURE:
<223> OTHER INFORMATION: Synthetic antibody

<400> SEQUENCE: 41
attgtgatca cccagtctcc agcaatcctg tctgcatctc caggggagaa ggtcacaatg         60
acttgcaggg ccagctcaag tgtaagttac atgcactggt accagcagaa gccaggatcc        120
tcccccaaac cctggattta tgccacatcc aacctggctt ctggagtccc tgctcgcttc        180
agtggcagtg ggtctgggac ctcttactct ctcacagtca gcagagtgga ggctgaagat        240
gctgccactt attactgcca gcagtggagt agtgacccat tcacgttcgg ctcgggggaca          300 aagttggaaa taaaac                                                                                              316

<210> SEQ ID NO 42
<211> LENGTH: 105
<212> TYPE: PRT
<213> ORGANISM: Artificial sequence
<220> FEATURE:
<223> OTHER INFORMATION: Synthetic antibody

<400> SEQUENCE: 42

Ile Val Ile Thr Gln Ser Pro Ala Ile Leu Ser Ala Ser Pro Gly Glu
1               5                   10                  15

Lys Val Thr Met Thr Cys Arg Ala Ser Ser Ser Val Ser Tyr Met His
                20                  25                  30

Trp Tyr Gln Gln Lys Pro Gly Ser Ser Pro Lys Pro Trp Ile Tyr Ala
            35                  40                  45

Thr Ser Asn Leu Ala Ser Gly Val Pro Ala Arg Phe Ser Gly Ser Gly
        50                  55                  60

Ser Gly Thr Ser Tyr Ser Leu Thr Val Ser Arg Val Glu Ala Glu Asp
65                  70                  75                  80

Ala Ala Thr Tyr Tyr Cys Gln Gln Trp Ser Ser Asp Pro Phe Thr Phe
                85                  90                  95

Gly Ser Gly Thr Lys Leu Glu Ile Lys
            100                 105

<210> SEQ ID NO 43
<211> LENGTH: 5
<212> TYPE: PRT
<213> ORGANISM: Artificial sequence
<220> FEATURE:
<223> OTHER INFORMATION: Synthetic antibody

<400> SEQUENCE: 43

Ser Ser Val Ser Tyr
1               5

<210> SEQ ID NO 44
<211> LENGTH: 15
<212> TYPE: DNA
<213> ORGANISM: Artificial sequence
<220> FEATURE:
<223> OTHER INFORMATION: Synthetic antibody

<400> SEQUENCE: 44
tcaagtgtaa gttac                                                                                    15

<210> SEQ ID NO 45
<211> LENGTH: 3
<212> TYPE: PRT
<213> ORGANISM: Artificial sequence
<220> FEATURE:
<223> OTHER INFORMATION: Synthetic antibody

<400> SEQUENCE: 45

Ala Thr Ser
1

<210> SEQ ID NO 46
<211> LENGTH: 9
<212> TYPE: DNA
<213> ORGANISM: Artificial sequence
<220> FEATURE:

<223> OTHER INFORMATION: Synthetic antibody

<400> SEQUENCE: 46 gccacatcc                                                                                9

<210> SEQ ID NO 47
<211> LENGTH: 9
<212> TYPE: PRT
<213> ORGANISM: Artificial sequence
<220> FEATURE:
<223> OTHER INFORMATION: Synthetic antibody

<400> SEQUENCE: 47

Gln Gln Trp Ser Ser Asp Pro Phe Thr
1               5

<210> SEQ ID NO 48
<211> LENGTH: 27
<212> TYPE: DNA
<213> ORGANISM: Artificial sequence
<220> FEATURE:
<223> OTHER INFORMATION: Synthetic antibody

<400> SEQUENCE: 48
cagcagtgga gtagtgaccc attcacg                                                             27

<210> SEQ ID NO 49
<211> LENGTH: 363
<212> TYPE: DNA
<213> ORGANISM: Artificial sequence
<220> FEATURE:
<223> OTHER INFORMATION: Synthetic antibody

<400> SEQUENCE: 49
aggtgaaact gcagcagtca ggacctgagc tggtgaagcc tggggcttca gtgaagatat        60
cctgtaaggc ttctggatac acgttcactg actactacat gaactgggtg aaggagagcc        120
atggaaagag ccttgagtgg attggagata ttaatcctaa caatggtggt tctacctact        180
acaaccagaa gttcaagggc aaggccacat tgactgtaga gaagtcctcc agcacagcct        240
tcatggagct ccgcagcctg acatctgagg actctgcagt ctattactgt gcaagatccc        300
tctacggtag tacctactac tttgactact ggggccaagg cacccctctc acagtctcct        360
cag                                                                       363

<210> SEQ ID NO 50
<211> LENGTH: 120
<212> TYPE: PRT
<213> ORGANISM: Artificial sequence
<220> FEATURE:
<223> OTHER INFORMATION: Synthetic antibody

<400> SEQUENCE: 50

Val Lys Leu Gln Gln Ser Gly Pro Glu Leu Val Lys Pro Gly Ala Ser
1               5                   10                  15

Val Lys Ile Ser Cys Lys Ala Ser Gly Tyr Thr Phe Thr Asp Tyr Tyr
                20                  25                  30

Met Asn Trp Val Lys Glu Ser His Gly Lys Ser Leu Glu Trp Ile Gly
            35                  40                  45

Asp Ile Asn Pro Asn Asn Gly Gly Ser Thr Tyr Tyr Asn Gln Lys Phe
        50                  55                  60

Lys Gly Lys Ala Thr Leu Thr Val Glu Lys Ser Ser Ser Thr Ala Phe
65                  70                  75                  80

```
Met Glu Leu Arg Ser Leu Thr Ser Glu Asp Ser Ala Val Tyr Tyr Cys
                85                  90                  95

Ala Arg Ser Leu Tyr Gly Ser Thr Tyr Tyr Phe Asp Tyr Trp Gly Gln
            100                 105                 110

Gly Thr Pro Leu Thr Val Ser Ser
        115                 120

<210> SEQ ID NO 51
<211> LENGTH: 8
<212> TYPE: PRT
<213> ORGANISM: Artificial sequence
<220> FEATURE:
<223> OTHER INFORMATION: Synthetic antibody

<400> SEQUENCE: 51

Gly Tyr Thr Phe Thr Asp Tyr Tyr
1               5

<210> SEQ ID NO 52
<211> LENGTH: 24
<212> TYPE: DNA
<213> ORGANISM: Artificial sequence
<220> FEATURE:
<223> OTHER INFORMATION: Synthetic antibody

<400> SEQUENCE: 52
ggatacacgt tcactgacta ctac                                          24

<210> SEQ ID NO 53
<211> LENGTH: 8
<212> TYPE: PRT
<213> ORGANISM: Artificial sequence
<220> FEATURE:
<223> OTHER INFORMATION: Synthetic antibody

<400> SEQUENCE: 53

Ile Asn Pro Asn Asn Gly Gly Ser
1               5

<210> SEQ ID NO 54
<211> LENGTH: 24
<212> TYPE: DNA
<213> ORGANISM: Artificial sequence
<220> FEATURE:
<223> OTHER INFORMATION: Synthetic antibody

<400> SEQUENCE: 54
attaatccta acaatggtgg ttct                                          24

<210> SEQ ID NO 55
<211> LENGTH: 13
<212> TYPE: PRT
<213> ORGANISM: Artificial sequence
<220> FEATURE:
<223> OTHER INFORMATION: Synthetic antibody

<400> SEQUENCE: 55

Ala Arg Ser Leu Tyr Gly Ser Thr Tyr Tyr Phe Asp Tyr
1               5                   10

<210> SEQ ID NO 56
<211> LENGTH: 39
<212> TYPE: DNA
<213> ORGANISM: Artificial sequence
<220> FEATURE:
```

-continued

<223> OTHER INFORMATION: Synthetic antibody

<400> SEQUENCE: 56
gcaagatccc tctacggtag tacctactac tttgactac                                       39

<210> SEQ ID NO 57
<211> LENGTH: 334
<212> TYPE: DNA
<213> ORGANISM: Artificial sequence
<220> FEATURE:
<223> OTHER INFORMATION: Synthetic antibody

<400> SEQUENCE: 57
gatattgtgc tgacccagtc tccagcttct ttggctgtgt ctctagggca gagggccacc       60
atctcctgca aggccagcca aagtgttgat tatgatggtg atagtttata gaactggtac       120
caacagaagc caggacagcc acccaaactc ctcatctatg ctgcatccaa tctagaatct       180
gggatcccag ccaggtttag tggcagtggg tctgggacag acttcactct caacatccat       240
cctgtggagg aggaggatgc tggaacctat tactgtcagc aaagtaatga cgatccgtgg       300
acgttcggtg gaggcaccaa gctggaaatc aaac                                     334

<210> SEQ ID NO 58
<211> LENGTH: 111
<212> TYPE: PRT
<213> ORGANISM: Artificial sequence
<220> FEATURE:
<223> OTHER INFORMATION: Synthetic antibody

<400> SEQUENCE: 58

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Gly Thr Tyr Tyr Cys Gln Gln Ser Asn
                85                  90                  95

Asp Asp Pro Trp Thr Phe Gly Gly Gly Thr Lys Leu Glu Ile Lys
            100                 105                 110

<210> SEQ ID NO 59
<211> LENGTH: 10
<212> TYPE: PRT
<213> ORGANISM: Artificial sequence
<220> FEATURE:
<223> OTHER INFORMATION: Synthetic antibody

<400> SEQUENCE: 59

Gln Ser Val Asp Tyr Asp Gly Asp Ser Tyr
1               5                   10

<210> SEQ ID NO 60
<211> LENGTH: 30
<212> TYPE: DNA
<213> ORGANISM: Artificial sequence
<220> FEATURE:
<223> OTHER INFORMATION: Synthetic antibody -continued

```
<400> SEQUENCE: 60
caaagtgttg attatgatgg tgatagttat                                    30

<210> SEQ ID NO 61
<211> LENGTH: 3
<212> TYPE: PRT
<213> ORGANISM: Artificial sequence
<220> FEATURE:
<223> OTHER INFORMATION: Synthetic antibody

<400> SEQUENCE: 61

Ala Ala Ser
1

<210> SEQ ID NO 62
<211> LENGTH: 9
<212> TYPE: DNA
<213> ORGANISM: Artificial sequence
<220> FEATURE:
<223> OTHER INFORMATION: Synthetic antibody

<400> SEQUENCE: 62 gctgcatcc                                                            9

<210> SEQ ID NO 63
<211> LENGTH: 9
<212> TYPE: PRT
<213> ORGANISM: Artificial sequence
<220> FEATURE:
<223> OTHER INFORMATION: Synthetic antibody

<400> SEQUENCE: 63

Gln Gln Ser Asn Asp Asp Pro Trp Thr
1               5

<210> SEQ ID NO 64
<211> LENGTH: 27
<212> TYPE: DNA
<213> ORGANISM: Artificial sequence
<220> FEATURE:
<223> OTHER INFORMATION: Synthetic antibody

<400> SEQUENCE: 64
cagcaaagta atgacgatcc gtggacg                                        27
```